US011883223B2

(12) United States Patent
Wang et al.

(10) Patent No.: US 11,883,223 B2
(45) Date of Patent: Jan. 30, 2024

(54) HEPATIC INFLAMMATION ANALYSIS WITH DYNAMIC PET

(71) Applicant: The Regents of the University of California, Oakland, CA (US)

(72) Inventors: Guobao Wang, Woodland, CA (US); Souvik Sarkar, Davis, CA (US); Ramsey D. Badawi, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 707 days.

(21) Appl. No.: 16/968,088

(22) PCT Filed: Feb. 15, 2019

(86) PCT No.: PCT/US2019/018239
§ 371 (c)(1),
(2) Date: Aug. 6, 2020

(87) PCT Pub. No.: WO2019/161220
PCT Pub. Date: Aug. 22, 2019

(65) Prior Publication Data
US 2021/0022697 A1 Jan. 28, 2021

Related U.S. Application Data

(60) Provisional application No. 62/630,982, filed on Feb. 15, 2018.

(51) Int. Cl.
*A61B 6/00* (2006.01)
*G16H 50/30* (2018.01)
(Continued)

(52) U.S. Cl.
CPC ............ *A61B 6/5217* (2013.01); *A61B 6/037* (2013.01); *A61B 6/481* (2013.01); *A61B 6/50* (2013.01);
(Continued)

(58) Field of Classification Search
CPC ....... A61B 6/5217; A61B 6/037; A61B 6/481; G16H 50/30
See application file for complete search history.

(56) References Cited

U.S. PATENT DOCUMENTS 10,223,610 B1 * 3/2019 Akselrod-Ballin ..... G06T 7/174
2009/0110256 A1 4/2009 Thielemans et al.
(Continued)

FOREIGN PATENT DOCUMENTS

CN 102317975 A 1/2012

OTHER PUBLICATIONS

Keramida, Georgia, et al. "Accumulation of 18F-FDG in the liver in hepatic steatosis." American Journal of Roentgenology 203.3 (2014): 643-648. (Year: 2014).*

(Continued)

*Primary Examiner* — Vincent Rudolph
*Assistant Examiner* — Raphael Schwartz
(74) *Attorney, Agent, or Firm* — Kilpatrick Townsend and Stockton LLP

(57) ABSTRACT

A system and method for determining kinetic parameters associated with a kinetic model of an imaging agent in a liver is provided. An image reconstruction device can receive radiotracer activities corresponding to a predetermined time period. For example, these radiotracer activities can include PET scan data corresponding to a number of time frames. The radiotracer activities can be used to determine a liver time activity curve and a circulatory input function. The liver time activity curve and circulatory input (Continued)

function can be used along with a kinetic model of the liver to produce kinetic parameters. These kinetic parameters can be used to determine hepatic scores, such as a hepatic steatosis score, a hepatic inflammation score, and a cirrhosis score. These scores are indicative of diseases of the liver, including nonalcoholic fatty liver disease, nonalcoholic steatohepatitis, and hepatic fibrosis.

19 Claims, 19 Drawing Sheets

(51) Int. Cl.
  *A61B 6/03* (2006.01)
  *G06T 7/00* (2017.01)
(52) U.S. Cl.
  CPC ........... *G06T 7/0016* (2013.01); *G16H 50/30* (2018.01); *A61B 6/486* (2013.01); *A61B 6/5205* (2013.01); *G06T 2207/10076* (2013.01); *G06T 2207/10104* (2013.01); *G06T 2207/30056* (2013.01)

(56) References Cited

U.S. PATENT DOCUMENTS

| | | | |
|---|---|---|---|
| 2014/0334702 | A1 | 11/2014 | El Fakhri et al. |
| 2015/0230762 | A1 | 8/2015 | Alpert et al. |
| 2017/0347986 | A1 | 12/2017 | Kohara et al. |

OTHER PUBLICATIONS

Rokugawa, Takemi, et al. "[18 F]-BMS-747158-02PET imaging for evaluating hepatic mitochondrial complex 1dysfunction in a mouse model of non-alcoholic fatty liver disease." EJNMMI research 7 (2017): 1-7. (Year: 2017).*
Radiological Society of North America Inc (RSNA): Radiation Dose in X-Ray and CT Exams, Radiological Society of North America, Available Online at https://www.radiologyinfo.org/en/info.cfm?pg=safety-xray, 2016, 5 pages.
Abele et al., Effect of Hepatic Steatosis on Liver FDG Uptake Measured in Mean Standard Uptake Values, Radiology, vol. 254, No. 3, Mar. 2010, pp. 917-924.
Abikhzer et al., Altered Hepatic Metabolic Activity in Patients with Hepatic Steatosis on FDG PET/CT, American Journal of Roentgenology, vol. 196, No. 1, Jan. 2011, pp. 176-180.
Angulo et al., Liver Fibrosis, but No Other Histologic Features, is Associated with Long-term Outcomes of Patients with Nonalcoholic Fatty Liver Disease, Gastroenterology, vol. 149, No. 2, Aug. 2015, 19 pages.
Arora et al., Non-invasive Diagnosis of Fibrosis in Non-alcoholic Fatty Liver Disease, Journal of Clinical and Experimental Hepatology, vol. 2, No. 2, Jun. 2012, pp. 145-155.
Bechmann et al., The Interaction of Hepatic Lipid and Glucose Metabolism in Liver Diseases, Hepatol, vol. 56, No. 4, Apr. 2012, pp. 952-964.
Bedossa et al., Biopsy and Noninvasive Methods to Assess Progression of Nonalcoholic Fatty Liver Disease, Gastroenterology, vol. 150, No. 8, Jun. 2016, pp. 1811-1822.
Ben-Haim et al., (18)F-FDG PET and PET/CT in the Evaluation of Cancer Treatment Response, Journal of Nuclear Medicine, vol. 50, No. 1, Jan. 2009, pp. 88-99.
Boellaard et al., FDG PET/CT: EANM Procedure Guidelines for Tumour Imaging: Version 2.0, European Journal of Nuclear Medicine and Molecular Imaging, vol. 42, No. 2, Feb. 2015, pp. 328-354.
Bohte et al., The Diagnostic Accuracy of US, CT, MRI and 1H-MRS for the Evaluation of Hepatic Steatosis Compared with Liver Biopsy: A Meta-Analysis, European Radiology, vol. 21, No. 1, Jan. 2011, pp. 87-97.
Borra et al., Inverse Association Between Liver Fat Content and Hepatic Glucose Uptake in Patients with Type 2 Diabetes Mellitus, Metabolism, vol. 57, No. 10, Oct. 2008, pp. 1445-1451.
Brix et al., Quantification of [(18)F] FDG Uptake in the Normal Liver Using Dynamic PET: Impact and Modeling of the Dual Hepatic Blood Supply, Journal of Nuclear Medicine, vol. 42, No. 8, Aug. 2001, pp. 1265-1273.
Brown et al., Histopathology of nonalcoholic fatty liver disease and nonalcoholic steatohepatitis, Metabolism, vol. 65, No. 8, Aug. 2016, pp. 1080-1086.
Brunt et al., Nonalcoholic Fatty Liver Disease (NAFLD) Activity Score and the Histopathologic Diagnosis in NAFLD: Distinct Clinicopathologic Meanings, Hepatology, vol. 53, No. 3, Mar. 2011, pp. 810-820.
Bural et al., Quantitative Assessment of the Hepatic Metabolic Volume Product in Patients with Diffuse Hepatic Steatosis and Normal Controls Through Use of FDG-PET and MR Imaging: A Novel Concept, Molecular Imaging and Biology, vol. 12, No. 3, Jun. 2010, pp. 233-239.
Chalasani et al., The Diagnosis and Management of Non-Alcoholic Fatty Liver Disease: Practice Guideline by the American Gastroenterological Association, American Association for the Study of Liver Diseases, and American College of Gastroenterology, Gastroenterology, vol. 142, No. 7, Jun. 2012, pp. 1592-1609.
Chen et al., Early Detection of Nonalcoholic Steatohepatitis in Patients with Nonalcoholic Fatty Liver Disease by Using MR Elastography, Radiology, vol. 259, No. 3, Jun. 2011, pp. 749-756.
Chen et al., Evaluation of Hepatocellular Carcinoma with Dynamic 11C-Acetate PET: A Dual-Modeling Method, IEEE Transactions on Nuclear Science, vol. 55, No. 3, Jun. 17, 2008, pp. 999-1007.
Chen et al., Noninvasive Quantification of the Cerebral Metabolic Rate for Glucose Using Positron Emission Tomography, 18F-Fluoro-2-Deoxyglucose, the Patlak Method, and an Image-Derived Input Function, Journal of Cerebral Blood Flow and Metabolism, vol. 18, No. 7, Jul. 1, 1998, pp. 716-723.
Filozof et al., Non-Alcoholic Steatohepatitis: Limited Available Treatment Options but Promising Drugs in Development and Recent Progress Towards a Regulatory Approval Pathway, Drugs, vol. 75, No. 12, 2015, pp. 1373-1392.
Fishbein et al., Hepatic MRI for Fat Quantitation: Its Relationship to Fat Morphology, Diagnosis, and Ultrasound, Journal of Clinical Gastroenterology, vol. 39, No. 7, Aug. 1, 2005, pp. 619-625.
Friedrich-Rust et al., Liver Fibrosis in Viral Hepatitis: Noninvasive Assessment with Acoustic Radiation Force Impulse Imaging versus Transient Elastography, Radiology, vol. 252, No. 2, Aug. 2009, pp. 595-604.
Gambhir, Molecular Imaging of Cancer With Positron Emission Tomography, Nature Reviews Cancer, vol. 2, No. 9, Sep. 2002, pp. 683-693.
Gastaldelli et al., Exenatide Improves Both Hepatic and Adipose Tissue Insulin Resistance: A Dynamic Positron Emission Tomography Study, Hepatology, vol. 64, No. 6, Dec. 2016, pp. 2028-2037.
Glatting et al., Choosing the Optimal Fit Function: Comparison of the Akaike Information Criterion and the F-Test, Medical Physics, vol. 34, No. 11, Nov. 2007, pp. 4285-4292.
Hashimoto et al., Characteristics and diagnosis of NAFLD/NASH, European Journal of Gastroenterology & Hepatology, vol. 28. No. S4, Dec. 2013, pp. 64-70.
Hjelkrem et al., Validation of the Non-alcoholic Fatty Liver Disease Activity Score, Alimentary Pharmacology & Therapeutics, vol. 34, No. 2, Jul. 2011, pp. 214-218.
Huwart et al., Liver Fibrosis: Non-Invasive Assessment with MR Elastography, NMR in Biomedicine, vol. 19, No. 2, Apr. 2006, pp. 173-179.
Iozzo et al., Effects of Metformin and Rosiglitazone Monotherapy on Insulin-Mediated Hepatic Glucose Uptake and Their Relation to Visceral Fat in Type 2 Diabetes, Diabetes Care, vol. 26, No. 7, Jul. 2003, pp. 2069-2074.
Iozzo et al., Fatty Acid Metabolism in the Liver, Measured by Positron Emission Tomography, is Increased in Obese Individuals, Gastroenterology, vol. 139, No. 3, Sep. 2010, pp. 846-856.

(56) References Cited

OTHER PUBLICATIONS

Iozzo et al., Insulin Stimulates Liver Glucose Uptake in Humans: An F-18-FDG PET Study, Journal of Nuclear Medicine, vol. 44, No. 5, May 2003, pp. 682-689.

Iozzo et al., Insulin-Mediated Hepatic Glucose Uptake is Impaired in Type 2 Diabetes: Evidence for a Relationship with Glycemic Control, The Journal of Clinical Endocrinology & Metabolism, vol. 28, No. 5, May 1, 2003, pp. 2055-2060.

Iozzo et al., Non-Esterified Fatty Acids Impair Insulin-Mediated Glucose Uptake and Disposition in the Liver, Diabetologia vol. 47, No. 7, Jul. 9, 2004, pp. 1149-1156.

Iozzo et al., Quantification of Liver Glucose Metabolism by Positron Emission Tomography: Validation Study in Pigs, Gastroenterology, vol. 132, No. 2, Feb. 2007, pp. 531-542.

Keiding et al., Bringing Physiology into PET of the Liver, Journal of Nuclear Medicine, vol. 53, No. 3, Mar. 2012, pp. 425-433.

Keramida et al., Accumulation of (18)F-FDG in the Liver in Hepatic Steatosis, American Journal of Roentgenology, vol. 203, No. 3, Sep. 2014, pp. 643-648.

Keramida et al., Hepatic Glucose Utilisation in Hepatic Steatosis and Obesity, Bioscience Reports, vol. 26, No. 6, Nov. 3, 2016, 8 pages.

Keramida et al., Hepatic Steatosis is Associated with Increased Hepatic FDG Uptake, European Journal of Radiology, vol. 83, No. 5, May 2014, pp. 751-755.

Keramida et al., Relationships of Body Habitus and SUV Indices with Signal-to-Noise Ratio of Hepatic F-18-FDG PET, European Journal of Radiology, vol. 85, No. 5, Mar. 3, 2016, 16 pages.

Kim et al., Association Between Noninvasive Fibrosis Markers and Mortality Among Adults with Nonalcoholic Fatty Liver Disease in the United States, Hepatology, vol. 57, No. 4, Apr. 2013, pp. 1357-1365.

Kleiner et al., Design and Validation of a Histological Scoring System for Nonalcoholic Fatty Liver Disease, Hepatology, vol. 41, No. 6, Jun. 2005, pp. 1313-1321.

Kleiner et al., Nonalcoholic Fatty Liver Disease: Pathologic Patterns and Biopsy Evaluation in Clinical Research, Seminars in Liver Disease, vol. 32, No. 1, Feb. 2012, pp. 3-13.

Kudomi et al., Non-Invasive Estimation of Hepatic Glucose Uptake From F-18 FDG PET Images Using Tissue-Derived Input Functions, European Journal of Nuclear Medicine and Molecular Imaging, vol. 36, No. 12, Dec. 2009, pp. 2014-2026.

Kwok et al., Screening Diabetic Patients for Non-alcoholic Fatty Liver Disease with Controlled Attenuation Parameter and Liver Stiffness Measurements: a Prospective Cohort Study, Gut, vol. 65, No. 8, 2015, pp. 1359-1368.

Lee et al., Radiologic Evaluation of Nonalcoholic Fatty Liver Disease, World Journal of Gastroenterology, vol. 20, No. 23, Jun. 21, 2014, pp. 7392-7402.

Lin et al., The Negative Impact of Fatty Liver on Maximum Standard Uptake Value of Liver on FDG PET, Clinical Imaging, vol. 35, No. 6, Nov.-Dec. 2011, pp. 437-441.

Loomba et al., Ezetimibe for the Treatment of Nonalcoholic Steatohepatitis: Assessment by Novel Magnetic Resonance Imaging and Magnetic Resonance Elastography in a Randomized Trial (MOZART Trial), Hepatology, vol. 61, No. 4, Apr. 2015, pp. 1239-1250.

Loomba et al., Magnetic Resonance Elastography Predicts Advanced Fibrosis in Patients with Nonalcoholic Fatty Liver Disease: A Prospective Study, Hepatology, vol. 60, No. 6, Dec. 2014, pp. 1920-1928.

Loomba et al., The Global NAFLD Epidemic, Nature Reviews Gastroenterology & Hepatology, vol. 10, No. 11, Nov. 2013, pp. 686-690.

Mariappan et al., Magnetic Resonance Elastography: A Review, Clinical Anatomy, vol. 23, No. 5, Jul. 2010, pp. 497-511.

Michelotti et al., NAFLD, NASH and Liver Cancer, Nature Reviews Gastroenterology and Hepatology, vol. 10, No. 11, Oct. 1, 2013, pp. 656-665.

Milic et al., Nonalcoholic Fatty Liver Disease/Steatohepatitis: Epidemiology, Pathogenesis, Clinical Presentation and Treatment, Digestive Diseases, vol. 30, No. 2, 2012, pp. 158-162.

Mishra et al., Abdominal Ultrasound for Diagnosis of Nonalcoholic Fatty Liver Disease (NAFLD), The American Journal of Gastroenterology, vol. 102, No. 12, Dec. 2007, pp. 2716-2717.

Munk et al., Liver Kinetics of Glucose Analogs Measured in Pigs by PET: Importance of Dual-Input Blood Sampling, Journal of Nuclear Medicine, vol. 42, No. 5, May 2001, pp. 795-801.

Musso et al., Meta-Analysis: Natural History of Non-Alcoholic Fatty Liver Disease (NAFLD) and Diagnostic Accuracy of Non-Invasive Tests for Liver Disease Severity, Annals of Medicine, vol. 43, No. 8, Dec. 2011, pp. 617-649.

Nalbantoglu et al., Role of Liver Biopsy in Nonalcoholic Fatty Liver Disease, World Journal of Gastroenterology, Jul. 21, 2014, pp. 9026-9037.

Noureddin et al., Utility of Magnetic Resonance Imaging Versus Histology for Quantifying Changes in Liver Fat in Nonalcoholic Fatty Liver Disease Trials, Hepatology, vol. 58, No. 6, Dec. 2013, pp. 1930-1940.

Pickhardt et al., Specificity of Unenhanced CT for Non-Invasive Diagnosis of Hepatic Steatosis: Implications for the Investigation of the Natural History of Incidental Steatosistigation of the Natural History of Incidental Steatosis, European Radiology, vol. 22, No. 5, Dec. 4, 2011, pp. 1075-1082.

Ratziu et al., Sampling Variability of Liver Biopsy in Nonalcoholic Fatty Liver Disease, Gastroenterology, vol. 128, No. 7, Jun. 1, 2005, pp. 1898-18906.

Reeder et al., Proton Density Fat-Fraction: A Standardized MR-Based Biomarker of Tissue Fat Concentration, Journal of Magnetic Resonance Imaging, vol. 36, No. 5, Nov. 2012, pp. 1011-1014.

Richard et al., Determination of an Optimal Pharmacokinetic Model of F-18-FET for Quantitative Applications in Rat Brain Tumors, Journal of Nuclear Medicine, vol. 58, No. 8, Aug. 2017, pp. 1278-1284.

Rinella et al., Nonalcoholic Fatty Liver Disease: A Systematic Review, JAMA the Journal of the American Medical Association, vol. 313, No. 22, Jun. 9, 2015, pp. 2263-2273.

Rockey et al., Liver Biopsy, Hepatology, vol. 49, No. 3, Mar. 2009, pp. 1017-1744.

Sanyal et al., Endpoints and Clinical Trial Design for Nonalcoholic Steatohepatitis, Hepatology, vol. 54, Issue 1, Jul. 2011, pp. 344-353.

Satapathy et al., Epidemiology and Natural History of Nonalcoholic Fatty Liver Disease, Seminars in Liver Disease, vol. 35, No. 3, Aug. 2015, pp. 221-235.

Schmidt et al., Kinetic Modeling in Positron Emission Tomography, Quarterly Journal of Nuclear Medicine, vol. 46, No. 1, Mar. 2002, pp. 70-85.

Tang et al., Nonalcoholic Fatty Liver Disease: MR Imaging of Liver Proton Density Fat Fraction to Assess Hepatic Steatosis, Radiology, vol. 267, No. 2, May 2013, pp. 422-431.

Tragardh et al., Methodologic Considerations for Quantitative 18F-FDG PET/CT Studies of Hepatic Glucose Metabolism in Healthy Subjects, Journal of Nuclear Medicine, vol. 56, No. 9, Sep. 2015, pp. 1366-1371.

Wang et al., Dynamic FDG-PET Study of Liver Inflammation in Non-Alcoholic Fatty Liver Disease, Journal of Hepatology, vol. 66, No. 1, Dec. 2017, p. S592.

Wang et al., PET Image Reconstruction Using Kernel Method, Institute of Electrical and Electronics Engineers Transactions on Medical Imaging, vol. 34, No. 1, Jan. 2015, pp. 61-71.

Weerdt et al., Image-Derived Input Functions for Determination of MRGlu in Cardiac 18F-FDG PET Scans, Journal of Nuclear Medicine, vol. 42, No. 11, Nov. 2001, pp. 1622-1629.

Winterdahl et al., Hepatic Blood Perfusion Measured by 3-Minute Dynamic F 18 FDG PET in Pigs, Journal of Nuclear Medicine, 2011, vol. 52, No. 7, Jul. 2011, pp. 1119-1124.

Wree et al., From NAFLD to NASH to Cirrhosis—New Insights into Disease Mechanisms, Nature Reviews Gastroenterology & Hepatology, vol. 10, No. 11, Nov. 2013, pp. 627-636.

Yang et al., Combined Serum Biomarkers in Non-Invasive Diagnosis of Non-Alcoholic Steatohepatitis, PLoS One, vol. 10, No. 6, Jun. 29, 2015, 14 pages.

(56) References Cited

OTHER PUBLICATIONS

Yeh et al., Pathological Features of Fatty Liver Disease, Gastroenterology, vol. 147, No. 4, Oct. 2014, pp. 754-764.
Yilmaz, Biomarkers for Early Detection of Non-alcoholic Steatohepatitis: Implications for Drug Development and Clinical Trials, Current Drug Targets, vol. 14, No. 11, Oct. 1, 2013, pp. 1357-1366.
Yin et al., Assessment of Hepatic Fibrosis with Magnetic Resonance Elastography, Clinical Gastroenterology and Hepatology, vol. 5, No. 10, Oct. 2007, pp. 1207-1213.
Zanotti-Fregonara et al., Population-Based Input Function and Image-derived Input Function for [11C](R)-Rolipram Pet Imaging: Methodology, Validation and Application to the Study of Major Depressive Disorder, Neuroimage, vol. 63, No. 3, Nov. 15, 2012, pp. 1532-1541.
First Office Action in Chinese Patent Appln. 201980013839.X dated Sep. 21, 2022 (English translation); 9 pages.
International Search Report and Written Opinion in PCT/US2019/018239 dated Jun. 10, 2019; 7 pages.
Gambhir S.S. et al.; "Tracer Kinetic Modeling Approaches for the Quanitification of Hepatic Function with Technetium-99m DISIDA and Scintigraphy"; *J. Nucl. Med.*; vol. 30, No. 9; Sep. 1989; pp. 1507-1518.
Kotasidis, F.A. et al.; "Advanced kinetic modelling strategies: towards adoption in clinical PET imaging"; *Clin. Transl. Imaging*; vol. 2; Jul. 2014; pp. 219-237.

\* cited by examiner

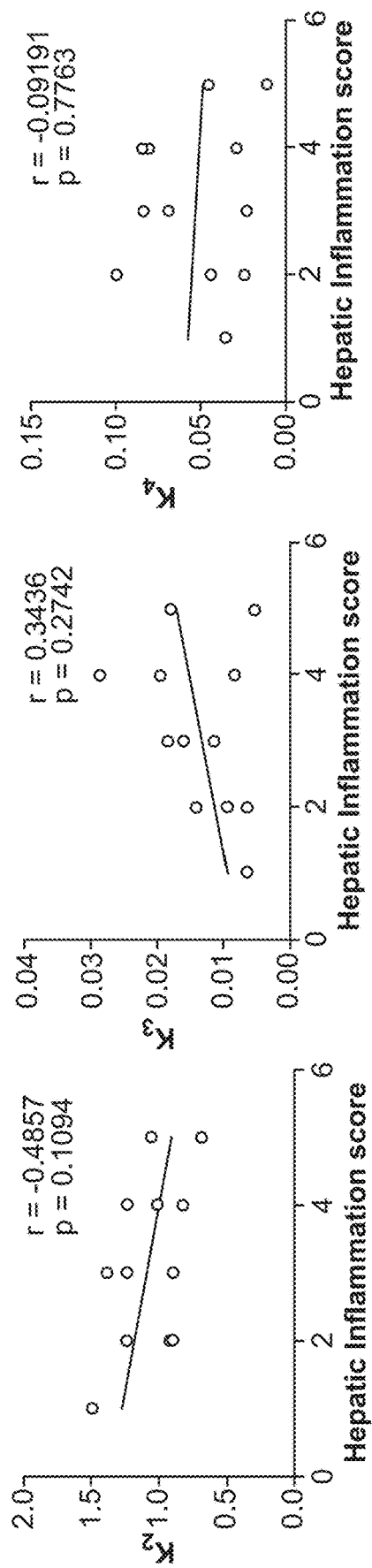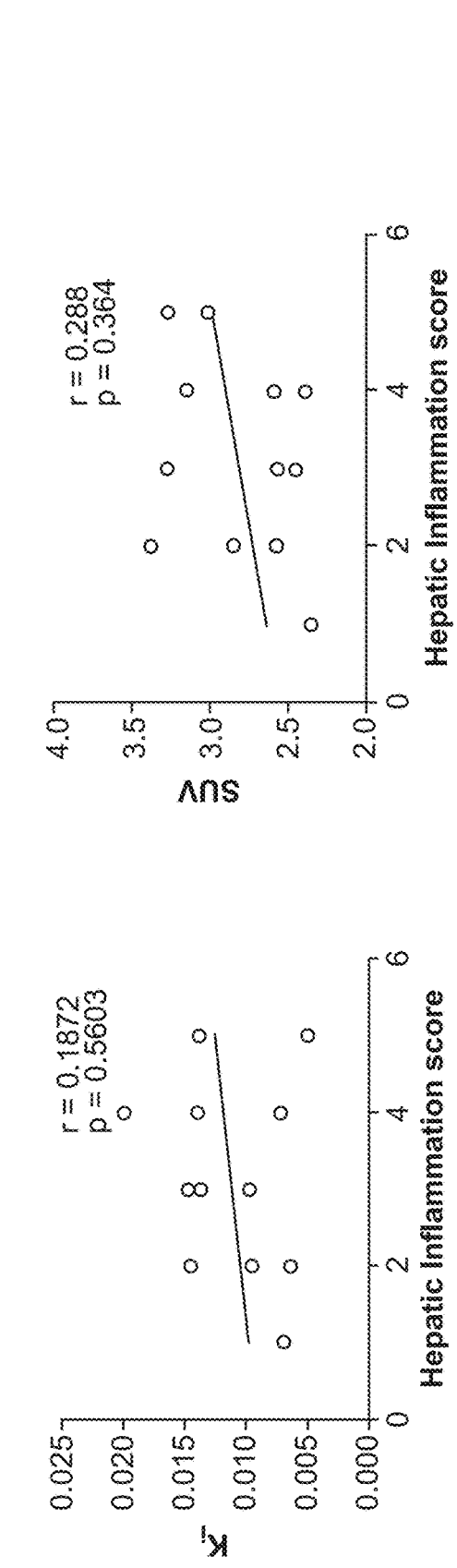
FIG. 16A  FIG. 16B  FIG. 16C  FIG. 16D  FIG. 16E

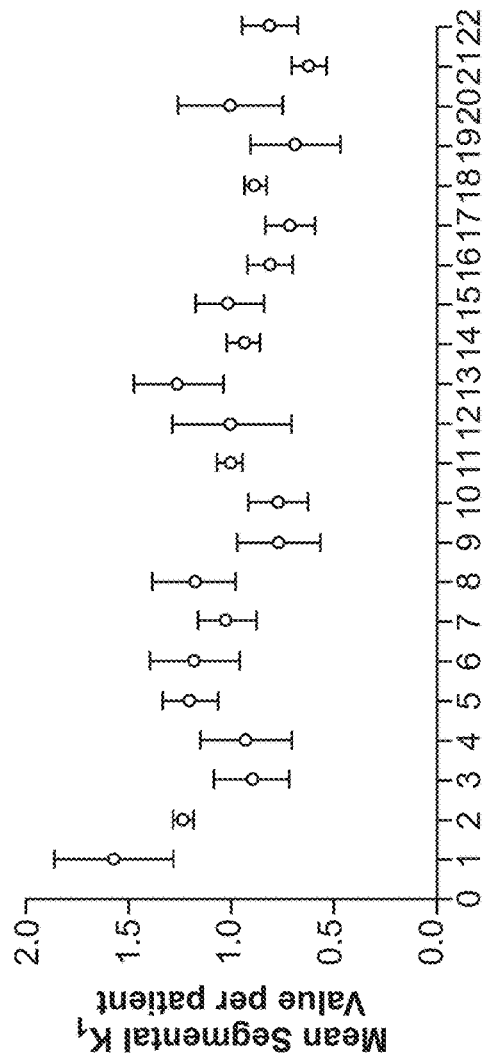
FIG. 24A
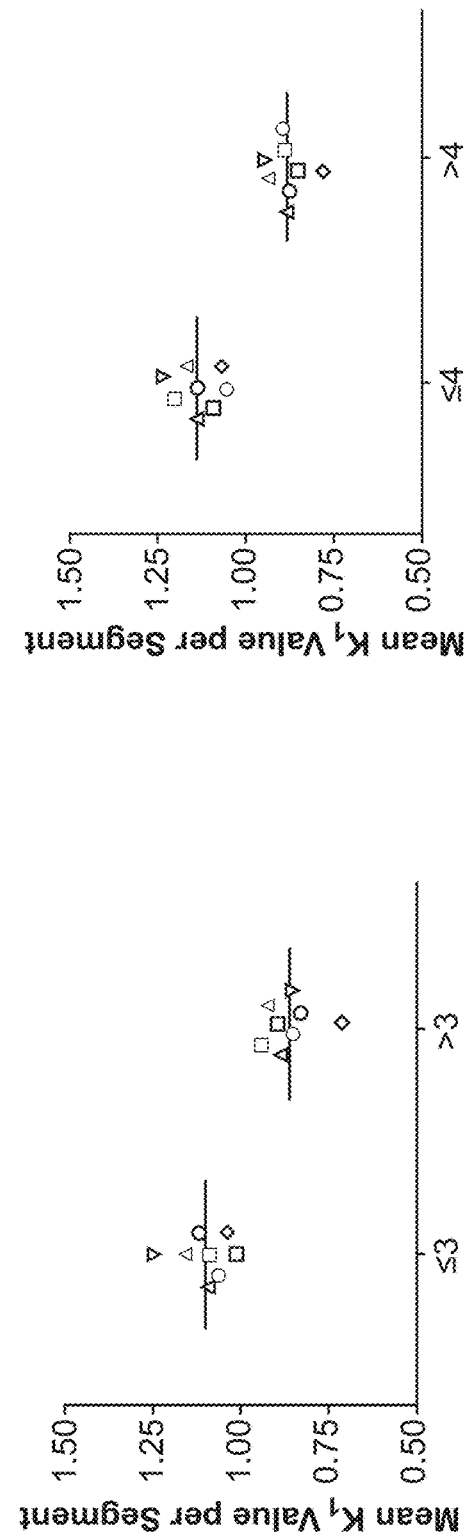
FIG. 24B
FIG. 24C

HEPATIC INFLAMMATION ANALYSIS WITH DYNAMIC PET

CROSS-REFERENCE TO RELATED APPLICATION

This application is a US National Phase Application Under Section 371 of PCT/US2019/018239, filed Feb. 15, 2019, which claims priority to U.S. Provisional Application No. 62/630,982, filed on Feb. 15, 2018, the contents of each of which are incorporated by reference herein in their entireties.

BACKGROUND

Nonalcoholic fatty liver disease (NAFLD) affects approximately 30% of the general population and is a leading cause of liver-related morbidity and mortality. NAFLD occurs when fat is deposited into the liver (steatosis) due to causes other than excessive alcohol use and is related to insulin resistance.

Nonalcoholic steatohepatitis (NASH) is a more severe form of NAFLD. Fat buildup in the liver leads to hepatocyte (liver cell) inflammation and injury. NASH can subsequently lead to cirrhosis, a condition where the liver does not function properly due to liver scarring (hepatic fibrosis), in addition to liver cancer and liver failure. Nash develops in 5-10% of NAFLD patients (i.e., 5-10 million people in the United States) and is associated with higher liver-related mortality than hepatic steatosis alone.

Identifying NASH, and differentiating NASH from NAFLD is an important part of patient management in NAFLD. There are currently no existing imaging techniques that can quantify live inflammation, which is essential for NASH assessment. Liver biopsy (extraction of tissue) followed by clinical histopathology (microscopic examination of extracted tissue) is the current conventional method of identifying hepatocellular inflammation.

However, there are a number of problems associated with liver biopsy. The procedure is invasive, and can result in pain at the biopsy site, bleeding, infection, or accidental injury to other organs in the body. Further, clinical histopathology requires processing of the tissue and analysis by an expert pathologist. This leads to a sizable delay between when the biopsy is performed and when the results are acquired, in many cases up to a week. Results may vary significantly depending on biopsy sample by proceduralist and between interpreting pathologists and introduce clinical errors in proper diagnosis.

SUMMARY

Embodiments provide for methods and systems for evaluating liver inflammation and associated conditions using tracer transport kinetic imaging, such as dynamic positron emission tomography (PET) scanning. An image reconstruction device can use the results of the tracer transport kinetic imaging to determine kinetic parameters associated with a kinetic model of an imaging agent in the liver, which may include, but is not limited to, first-pass perfusion imaging. The image reconstruction device can generate hepatic scores, such as a liver inflammation score that characterizes NASH in patients, based on one or more of the kinetic parameters.

Embodiments provide for a novel, imaging-based method of characterizing liver inflammation that is both safer and quicker than conventional liver biopsy. PET scanning as an exemplary tracer transport kinetic imaging method is a non-invasive procedure and avoids many of the complications (e.g., pain, bleeding, infection, etc.) that may occur during a biopsy. Additionally, unlike clinical histopathology, embodiments can provide results immediately after performing the PET scan, rather than a week later, as in the case of biopsy.

One embodiment is directed to a method of determining one or more kinetic parameters associated with a kinetic model of an imaging agent in a liver, performed by an image reconstruction device. The image reconstruction device receives a plurality of imaging agent activities corresponding to a predetermined time period. The image reconstruction device determines a liver time activity curve and a circulatory input function based on the plurality of imaging agent activities. The image reconstruction device determines one or more kinetic parameters associated with the kinetic model of the imaging agent in the liver based on the liver time activity curve and the circulatory input function.

Another embodiment is directed to a system comprising an image reconstruction device. The image reconstruction device comprises a processor and a non-transitory computer readable medium coupled to the processor, the non-transitory computer readable medium comprising code executable by the processor for performing the above-noted method.

These and other embodiments are described in further detail below.

Terms

Prior to discussing specific embodiments, some terms may be described in detail.

A "memory" is any suitable device or devices that may store electronic data. A suitable memory may comprise a non-transitory computer readable medium that stores instructions that can be executed by a processor to implement a desired method. Examples of memories may comprise one or more memory chips, disk drives, etc. Such memories may operate using any suitable electrical, optical, and/or magnetic mode of operation.

A "processor" is any suitable data computation device or devices. A processor may comprise one or more microprocessors working together to accomplish a desired function. The processor may include a CPU that comprises at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

An "imaging agent" may refer to a chemical compound that can be administered to human body and traced using tracer transport kinetic imaging techniques. For example, the imaging agent can be traced due to radioactive decay. Exemplary imaging agents may include radiotracers and contrast agents. According to various embodiments, a radiotracer may be used in connection with positron emission tomography (PET) imaging, and contrast agents such as an iodone-based agent may be used in connection with computerized tomography (CT) imaging, contrast agents such as a gadolinium-based agent may be used in connection with a Magnetic resonance imaging (MRI).

A "radiotracer," "radioactive tracer," or "radioactive label" is a chemical compound that can be traced due to radioactive decay. A radiotracer may be a chemical compound in which one or more atoms have been replaced by a radioisotope. A radiotracer may be used as part of a medical imaging system, such as positron emission tomography (PET). $^{18}$F-flourodeoxyglucose (FDG) is an example of a radiotracer. A radiotracer may have an associated radioactive dose, e.g., 10 mCi, and may be detectable by a medical imaging system or scanning device, such as a PET scanner.

"Imaging agent activity" or "radiotracer activity" may refer to a radioactivity of an imaging agent such as a radiotracer. Radiotracer activity may also refer to radioactivity of a radiotracer in some volume. For example, the radiotracer activity (e.g., 0.01 mCi) of one mL of liver tissue. Radiotracer activity may also refer to the radioactivity of a radiotracer during a time period or time frame. For example, the total radiotracer activity of one mL of liver tissue over a thirty second time frame. Radiotracer activity may also refer to a radiotracer activity statistic, such as the average radiotracer activity or standard deviation of radiotracer activity in a volume of tissue during a time frame.

A "scanning device" is a device that can detect imaging agent activity (or radiotracer activity). A PET scanner is an example of a scanning device. A scanning device may contain a "detector ring" comprising "detector blocks." The detector blocks may further comprise scintillator crystals and a photomultiplier. The detector ring may be used by the scanning device to detect events or activities, such as a gamma photo striking a scintillator.

A "coincidence processing device" is a device that can resolve, process, or interpret data recording by a scanning device. For example, a coincidence processing device may be a computer or other hardware that receives signals, such as time-varying currents or voltages from a scanning device, and determines whether those currents or voltages correspond to coincidence events, such as pairs of gamma photons striking opposite, or near opposite detector blocks at nearly the same time.

An "image reconstruction device" is a device that can reconstruct images from radiotracer activity. An image reconstruction device can produce a three (or more) dimensional model of radiotracer activity in space and time. For example, an image reconstruction device can be used to produce a model showing FDG activity in a liver over a period of time. An image reconstruction device can also calculate radiotracer statistics, such as the average FDG activity in a given region of interest, or a liver time activity curve and circulatory input function. The image reconstruction device can determine kinetic parameters associated with a kinetic model of a radiotracer in the liver based on these radiotracer statistics. Further, an image reconstructing device can generate a number of hepatic scores based on kinetic parameters and other statistics, such as liver SUVR. An image reconstruction device may be in communication with a coincidence processing device, and may receive radiotracer activities from the coincidence processing device. An image reconstruction device may be a computer, such as a desktop or laptop computer.

A "region of interest" (ROI) is a volume over which statistics can be calculated. As an example, a region of interest may be a volume of liver or circulatory tissue over which total or average radiotracer activity can be calculated. A region of interest, or regions of interest may be used to estimate or relate a statistic to a statistic corresponding to a larger volume. For example, a number of regions of interest in different volumes of liver tissue may be used to estimate radiotracer activity throughout the entire liver.

A "time activity curve" is radiotracer activity as a function of time. For example, a time activity curve can be a function characterizing FDG activity in the liver as a function of time. A time activity curve may be derived or estimated from data using curve fitting.

An "input function" is a function describing the input of some process. For example, an input function can be a function of time relating the flow or "input" of blood (in the case of a circulatory input function) to an organ such as the liver.

A "standardized uptake value" (SUV) is a ratio of radiotracer activity within a volume of tissue to total radiotracer activity throughout the body. For example, the standardized uptake value of the liver can be the radiotracer activity detected in the liver (for example, using a PET scan) over the radiotracer activity in the entire body. The radiotracer activity in the entire body may be determined as a ratio of the injected dosage and the weight of the patient. The standardized uptake value can be measured in g/mL, or as a unitless quantity in soft tissue with approximate mass density 1 g/mL.

A "standardized uptake value ratio" (SUVR) is a ratio of standardized uptake values. For example, the standardized uptake value ratio could be the ratio of the standardized uptake value of the liver to the standardized uptake value of blood. The standardized uptake value ratio is a unitless quantity and can account for body factors.

A "kinetic model" is a model describing the movement of something. For example, a kinetic model may be a compartment model describing the movement of a radiotracer such as FDG between a blood supply and hepatic tissue cells. A kinetic model may be characterized by kinetic parameters.

A "kinetic parameter" is a parameter used to characterize a kinetic model. For example, a kinetic parameter can be a rate constant, indicating the rate at which something (e.g., a imaging agent) flows between compartments in a compartment model, such as the rate at which the imaging agent flows from a bloodstream into a hepatic tissue cell.

A "fractional blood volume" ($v_b$) is the proportion of blood volume in some volume of tissue. For example, $v_b$ may refer to the proportion of blood outside the liver, and its complement, $1-v_b$, may refer to the proportion of blood inside liver tissue. The fractional blood volume can be used as a kinetic parameter that characterizes a kinetic model of a radiotracer (such as FDG) in the liver.

A "blood to hepatic tissue rate" ($K_1$) is the rate at which a imaging agent in blood flows into hepatic tissue cells (hepatocytes). For example, a blood to hepatic tissue rate may refer to the rate at which FDG is transported from the blood to hepatic tissue by glucose transporters. The blood to hepatic tissue rate can be used as a kinetic parameter that characterizes a kinetic model of a imaging agent in the liver.

A "hepatic tissue to blood rate" ($k_2$) is the rate at which a imaging agent in blood moves from hepatic tissue cells to the blood stream. The hepatic tissue to blood rate can be used as a kinetic parameter that characterizes a kinetic model of a imaging agent in the liver.

A "phosphorylation rate" ($k_3$) is the rate at which a molecule is phosphorylated. As an example, a phosphorylation rate may refer to the rate at which FDG in the liver is phosphorylated by hexokinase into FDG-6-Phosphate (FDG-6P). The phosphorylation rate can be used as a kinetic parameter that characterizes a kinetic model of a imaging agent in the liver.

A "dephosphorylation rate" ($k_4$) is the rate at which a molecule is dephosphorylated. As an example, a dephosphorylation rate may refer to the rate at which FDG-6P in the liver is dephosphorylated into FDG. The dephosphorylation rate can be used as a kinetic parameter that characterizes a kinetic model of a imaging agent in the liver.

A "portal vein rate" ($k_a$) is the rate at which a imaging agent in blood flows through the gastrointestinal system before entering the liver through the portal vein. The portal vein rate can be used as a kinetic parameter that characterizes a kinetic model of a imaging agent in the liver.

A "hepatic artery fraction" ($f_A$) is the fraction of a imaging agent in blood that flows into the liver via the hepatic artery, as opposed to the portal vein. The hepatic artery fraction can be used as a kinetic parameter that characterizes a kinetic model of a imaging agent in the liver.

A "hepatic steatosis score" is a score characterizing hepatic steatosis. For example, the hepatic steatosis score may correspond to the steatosis score of the NASH-CRN criteria or another scoring schema. The hepatic steatosis score may have a defined range (e.g., 0-3), and can be further characterized based on the value of the score. For example, a score of 0 or 1 may correspond to "low steatosis," a score of 2 may correspond to "medium steatosis," and a score of 3 may correspond to "high steatosis."

A "hepatic inflammation score" is a score characterizing hepatic inflammation. For example, the hepatic inflammation score may correspond to the lobular inflammation score and hepatocyte ballooning score of the NASH-CRN criteria or another scoring schema. The hepatic inflammation score may have a defined range (e.g., 0-5), and can be further characterized based on the value of the score. For example, a score of 0-2 may correspond to "low inflammation," a score of 3 may correspond to "medium inflammation," and a score of 4-5 may correspond to "high inflammation."

A "hepatic fibrosis score" is a score characterizing hepatic fibrosis. For example, a hepatic fibrosis score may correspond to a fibrosis stage as defined by the NASH-CRN criteria or another scoring or staging schema. The hepatic fibrosis score may have a defined range (e.g., 0-4).

BRIEF DESCRIPTION OF THE DRAWINGS

FIG. 16A shows a correlation between kinetic parameter $k_2$ and hepatic inflammation, according to various embodiments.

FIG. 16B shows a correlation between kinetic parameter $k_3$ and hepatic inflammation, according to various embodiments.

FIG. 16C shows a correlation between kinetic parameter $k_4$ and hepatic inflammation, according to various embodiments.

FIG. 16D shows a correlation between kinetic parameter $K_i$ and hepatic inflammation, according to various embodiments.

FIG. 16E shows a correlation between liver standardized uptake value and hepatic inflammation, according to various embodiments.

FIG. 24A shows the mean (plus or minus variation) in K1 among the eight segments in each of the 22 patients, according to various embodiments.

FIG. 24B shows a distinct segregation among those with low or high inflammation, according to various embodiments.

FIG. 24C shows a distinct segregation among those with low and high NAS (with a low NAS of ≤4 and a high NAS of >4), according to various embodiments.

DETAILED DESCRIPTION

Figure 1:
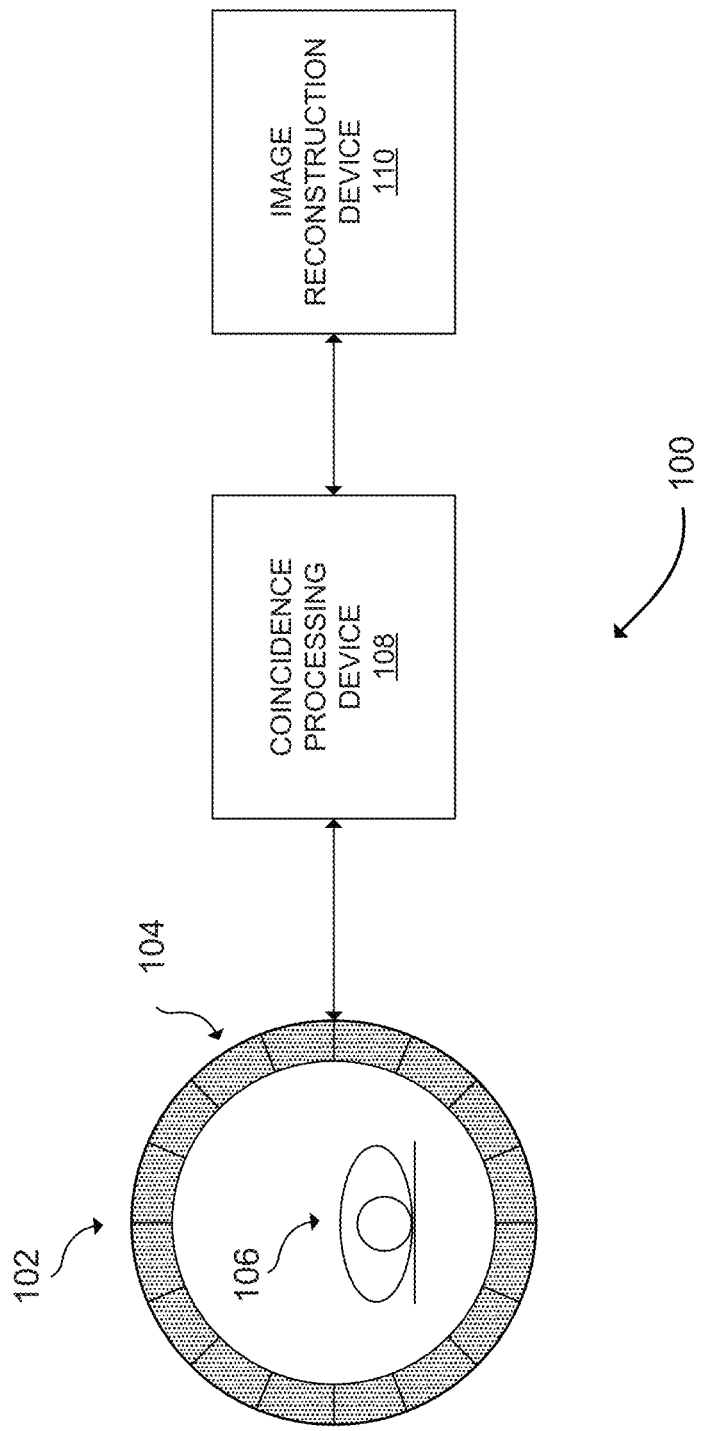
FIG. 1 shows a block diagram of an exemplary system according to some embodiments.

Embodiments relate to methods and systems for determining one or more kinetic parameters associated with a kinetic model of an imaging agent in a liver. These kinetic parameters can be used to determine hepatic scores that can be used to evaluate NAFLD and NASH in patients. The kinetic parameters can be determined by an image reconstruction device based on a plurality of imaging agent activities, which can be collected, for example, as part of a tracer transport kinetic imaging technique including but not limited to a PET scan, a computerized tomography (CT) scan, a Magnetic resonance imaging (MRI), etc. Embodiments are discussed below in connection with a PET scan. However, embodiments are not limited to the use of PET scan and other dynamic tracer transport kinetic imaging techniques may be used in connection with various embodiments.

The kinetic model of the imaging agent in the liver describes how the imaging agent is expected to move through the liver and surrounding tissue, including the circulatory system. Embodiments are discussed in connection with the exemplary radiotracer $^{18}$F-flourodeoxyglucose (FDG) used in connection with PET imaging. However, embodiments are not limited to the use of FDG and other types of radiotracers or imaging agents may be used in connection with the tracer kinetic modeling method discussed herein. FDG, for example, is absorbed from the bloodstream by hepatic tissue cells, and is also released by hepatic tissue cells into the bloodstream. The rate at which these processes occur is described by the kinetic rate parameters $K_1$ and $k_2$ respectively. Additionally, FDG in hepatic cells is phosphorylated into FDG-6P (leading to a decrease in hepatic cell FDG) and FDG-6P is dephosphorylated into FDG (leading to an increase in hepatic cell FDG). The rate at which these processes occur is described by the kinetic rate parameters $k_3$ and $k_4$ respectively. These kinetic parameters partially characterize the kinetic model of the imaging agent in the liver.

The image reconstruction device can determine these kinetic parameters based off the plurality of imaging agent activities, which, in turn, may be determined by analyzing the tracer transport kinetic imaging data. The imaging agent activities may be used to generate a liver time activity curve (TAC) and a circulatory input function. The image reconstruction device can use the liver TAC, circulatory input function, and kinetic model to jointly estimate the kinetic parameters. Additionally, the image reconstruction device can calculate a liver SUV and liver SUVR based on the imaging agent activities.

In some embodiments, the image reconstruction device can use these kinetic parameters, along with the SUV and the SUVR in order to generate hepatic scores, which may correspond to scores associated with the NASH-CRN criteria or another scoring scheme.

In summary, embodiments provide for systems and methods for producing kinetic parameters associated with a kinetic model of a imaging agent in a liver. These kinetic parameters can be used to produce hepatic scores that characterize steatosis, inflammation, and fibrosis of the liver.

FIG. 1 shows a block diagram of an exemplary system 100 comprising a scanning device 102, coincidence processing device 108, and an image reconstruction device 110. In some embodiments, the scanning device 102 may be a PET scanner, and may comprise a ring of detector blocks 104. Additionally shown is a patient 106.

The scanning device 102 can detect imaging agent activity corresponding to imaging agents (e.g. radiotracers) in the patient 106. During or prior to a scanning procedure, the patient 106 is injected with an imaging agent. The imaging agent undergoes radioactive decay while inside the patient 106. Radioactive decay results in the imaging agent emitting a positron, the anti-particle of an electron. The positron moves a short distance (e.g., one millimeter) throughout the patient's 106 body before encountering an electron. When the positron encounters the electron, the positron electron pair is annihilated, generating two 511 keV gamma photons with approximately opposite velocity. These gamma photons travel through the patient 106 before striking opposite or near opposite detector blocks 104 of the scanning device 102.

The detector blocks 104 may comprise a number of scintillators and photomultiplier tubes. The scintillators give off light when struck by ionizing radiation (e.g., gamma photons). Photomultiplier tubes multiply the current produced by incident light (i.e., from the scintillator). These current signals can be passed to the coincidence processing device 108.

The coincidence processing device 108 comprises any suitable hardware for processing signals from the scanning device 102. As an example, the coincidence processing device 108 receives current signals from the scanning device 102 and evaluate "coincidence events," events corresponding to opposite detector blocks 104 generating a current at nearly the same time (e.g., within six to twelve nanoseconds of one another). These coincidence events correspond to paired gamma photons striking the detector blocks 104, and consequently correspond to the generation of those gamma photons and the positron emission by the imaging agent. Each coincidence event can represent a line of response (LOR) that connects two detector blocks 104 along the positron emission.

The data produced by the coincidence processing device 108 may be referred to as "imaging agent activity data" or a "plurality of imaging agent activities." It can be represented as sinograms or list mode data and provided to the image reconstruction device 110 for reconstruction.

The image reconstruction device 110 comprises any suitable hardware for reconstructing images from a plurality of imaging agent activities. In some embodiments, the hardware includes a processor and a computer readable medium comprising code, executable by the processor for performing image reconstruction related functions and other functions. The image reconstruction device 110 can use any suitable display method to generate an image representation of the plurality of imaging agent activities. As an example, expectation-maximization methods, such as ordered subsets expectation maximization (OSEM) or Shepp-Vardi. As another example, Bayesian methods such as sieve estimation. The image representation can be a three or more dimensional image, comprising a number of voxels. For example, a voxel may represent imaging agent activity within a 1 mm×1 mm×1 mm cube over a plurality of time frames. The entire collection of voxels forming the image can represent imaging agent activity throughout the liver and surrounding tissue over the time frames.

In some embodiments, the image reconstruction device 110 can define regions of interest (ROI). An ROI can be a collection of voxels, either contiguous or otherwise, that define a region over which statistics can be calculated. As an example, a region of interest can be a collection of voxels within a 25 mm diameter sphere. The region of interest may be used to calculate imaging agent activity statistics within that region, e.g., the total imaging agent activity within the ROI over a given time frame, the average or running average imaging agent activity within the ROI, etc.

In some embodiments, the image reconstruction device 110 can determine time activity curves, circulatory input functions, kinetic parameters, SUVs, SUVRs, as well as hepatic scores such as hepatic inflammation, hepatic steatosis, and hepatic fibrosis scores. The image reconstruction device 110 will be discussed in further detail below with references to FIGS. 2-4.

Figure 2:
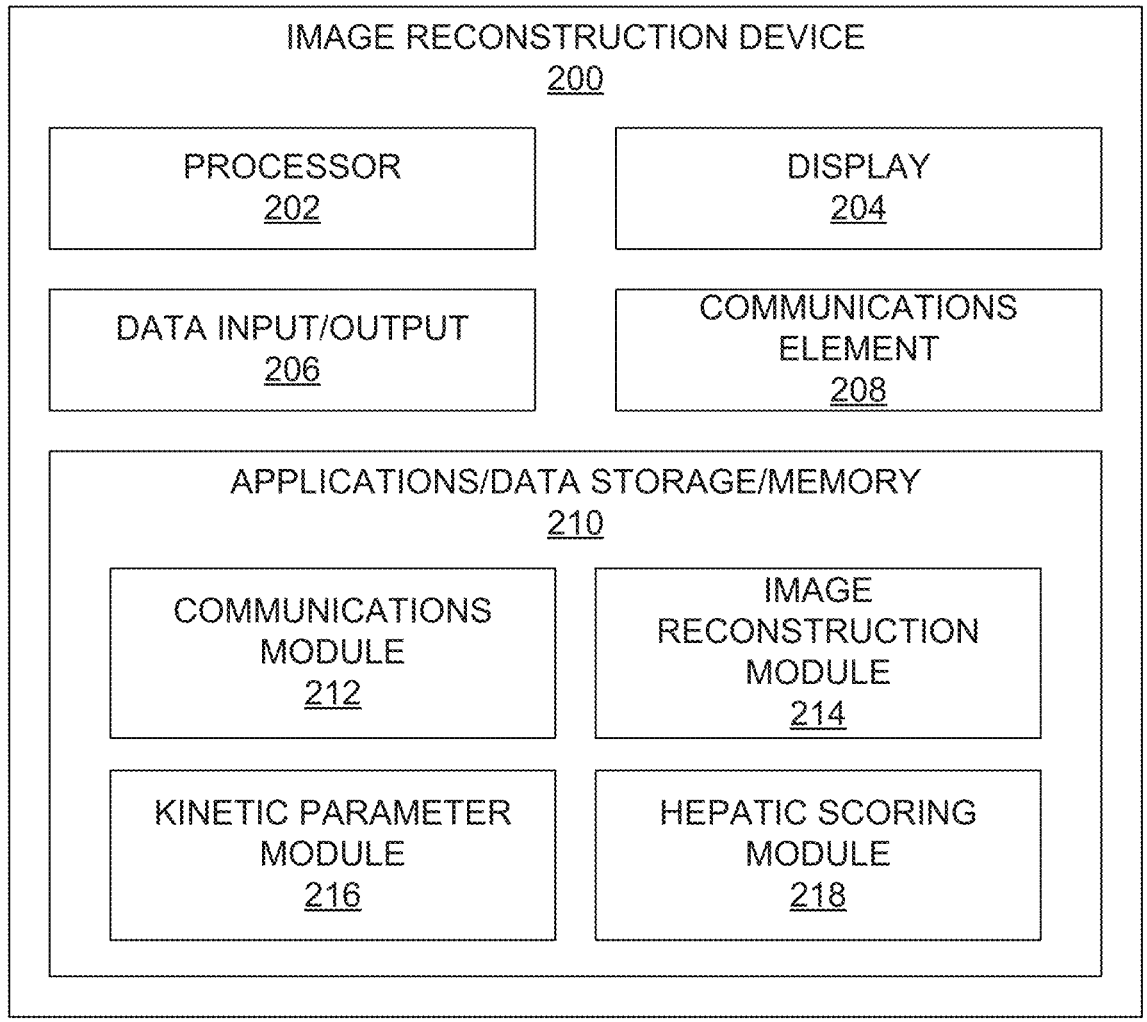
FIG. 2 shows a block diagram of an exemplary image reconstruction device according to some embodiments.

FIG. 2 shows an exemplary image reconstruction device 200 according to some embodiments. The image reconstruction device 200 comprises a processor 202, a display 204, a data input/output component 206, a communications element 208, and a data storage component 210 comprising a communications module 212, an image reconstruction module 214, a kinetic parameter module 216, and a hepatic scoring module 218.

The image reconstruction device 200 includes circuitry that is used to enable certain device functions, such as constructing images based on imaging agent activity data or a plurality of imaging agent activities, determining kinetic parameters, determining hepatic scores, or issuing an alert. The functional elements responsible for enabling those functions include a processor 202 that can execute instructions that implement the functions and operations of the image reconstruction device 200. Processor 202 can access data storage 210 (or another suitable memory region or element) to retrieve instructions or data used in executing the instructions, such as statistical analysis scripts or applications. Data input/output elements 206, such as a keyboard, mouse, touchscreen, etc., enables a user to operate the image reconstruction device 200 and input data (e.g., sampling conditions, OSEM iterations or subsets, ROI parameters, injected dose, patient weight, etc.) Data input/output elements can be configured to output data (via a speaker, for example). Display 204 can be used to output data to a user or issue an alert to a user. The communications element 208 (such as a communications interface like USB, PS/2, a wireless communications interface, etc.) can enable data transfer between the image reconstruction device 200 and other devices, such as the coincidence processing device 108 or another device in a network (such as a computer in a local area network).

Communications module 212 can enable data transfer between the image reconstruction device 200 and other devices, such as the coincidence processing device 108 or other devices or computers over a network, such as a local area network (LAN) or a network such as the Internet.

The image reconstruction module 214 comprises code enabling the processor 202 to generate images from a plurality of imaging agent activities. These imaging agent activities can be received by the image reconstruction device 200 from the coincidence processing device 108 using the communications element 208 and communications module 212. The image reconstruction module 214 can enable the processor 202 to generate three or more dimensional models based on these imaging agent activities, using any number of appropriate reconstruction methods. The image reconstruction module 214 can include code enabling the processor to display a graphical user interface (GUI) on the display 204, allowing a user of the image reconstruction device to interact with the image via data input/output 206. For example, the GUI can enable the user to define regions of interest using free-hand drawing or using shapes (such as a sphere or rectangular prism). The graphical user interface may also allow the user to redefine image reconstruction parameters, such as the number of iterations and number of subsets in an image reconstruction method such as OSEM.

Further, the image reconstruction module 214 comprises code or instructions enabling the processor 202 to calculate statistics over a region of interest or regions of interest. For example, the total imaging agent activity in that region of interest over a time period or the average imaging agent activity in that region of interest. Additionally, the image reconstruction module 214 enables the processor to calculate statistics based on a number of regions of interest, e.g., the difference in total or average imaging agent activity between two regions of interest, or the sum or average imaging agent activity across multiple regions of interest.

Additionally, the image reconstruction module 214 comprises code or instructions enabling the generation of time activity curves (TAC) describing imaging agent activity in one or more voxels or regions of interest over a period of time. The image reconstruction device may generate time activity curves using any number of suitable methods, including regression analysis, and will be discussed in further detail below. The image reconstruction module 214 can comprise code enabling graphical display of time activity curves. Further, the image reconstruction module 214 can comprise code enabling the determination of input functions, such as circulatory input functions based on imaging agent activity in circulatory regions of interest, or based on time activity curves generated from imaging agent activity in circulatory regions of interest.

The kinetic parameter module 216 comprises code or instructions enabling the processor 202 to determine kinetic parameters associated with a kinetic model of an imaging agent in a liver. The image reconstruction device 200 can determine a kinetic or compartmental model describing the liver, either based on a model or parametric relationship stored on data storage 210. The kinetic parameter module 216 can comprise code enabling a user to input or define a model via data input/output 206. The kinetic parameter module 216 can comprise code enabling the processor to perform any number of appropriate methods for determining kinetic parameters based on a time activity curve. For example, the kinetic parameter module 216 can comprise code enabling joint parameter estimation based on least squares curve fitting, such as the Levenberg-Marquardt or damped least-squares method. The kinetic parameter module 216 additionally comprises code enabling the calculation of liver SUV and liver SUVR based on imaging agent activities.

The hepatic scoring module 218 comprises code enabling the processor 202 to determine one or more hepatic scores, including a hepatic inflammation score, a hepatic steatosis score, and a hepatic fibrosis score based on the kinetic parameters, liver SUV, and liver SUVR. As an example, the hepatic scoring module 218 can comprise a database or lookup table that relates kinetic parameters, SUV, or SUVR to hepatic inflammation, hepatic steatosis, or hepatic fibrosis. The hepatic scoring module can also comprise code defining a functional relationship between these scores, the liver SUV, and the liver SUVR.

Further, the hepatic scoring module 218 comprises code enabling the processor 202 to compare hepatic scores to predetermined thresholds and issue an alert when one or more hepatic scores exceeds predetermined thresholds.

As an example, an alert can be a visual indicator appearing on the display 204, such as a pictographical or symbolic (e.g., an exclamation point or a large "X") display. As another example, an alert may be a displayed message, such as "the hepatic inflammation score exceeds a safe threshold." An alert can comprise an audio tone produced by a speaker, buzzer, etc., via the data input/output 206. As another example the alert can comprise an electronic message transmitted to another device via communications element 208 and the communications module 212, such as an email message transmitted to a computer via the Internet, or a message transmitted and stored in a server database. The alert message can include any relevant information regarding the alert, such as the hepatic scores, threshold values, patient characteristics (such as height, weight, gender, etc.), imaging agent activity data, dosage, etc.

In some embodiments, the data storage 210 comprises code executable by the processor 202 for performing a method. The method comprises the image reconstruction device 200 receiving a plurality of imaging agent activities corresponding to a predetermined time period. In some embodiments, the plurality of imaging agent activities are received from a coincidence processing device. The image reconstruction device 200 determines a liver time activity curve and circulatory input function based on the plurality of imaging agent activities. Further, the image reconstruction device determines one or more kinetic parameters associated with a kinetic model of an imaging agent in a liver.

According to various embodiments, the image reconstruction device 200 generates an output characterizing liver inflammation in the liver based on the one or more kinetic parameters. For example the image reconstruction device 200 may generate an output indicating the presence (or absence) of nonalcoholic fatty liver disease (NAFLD) and/or nonalcoholic steatohepatitis (NASH) in the liver. According to various embodiments, the output may be a visual (e.g. printed or displayed, such as a report, an image or a graph) or audible (e.g. played, such as an alarm, a sound or spoken word(s)) output indicating the presence or absence of NAFLD or NASH in the liver. According to some embodiments, the output may be transmitted to an electronic device. In some embodiments, the output may be further analyzed to make the determination of the NAFLD or NASH in the liver.

In some embodiments, the method further comprises the image reconstruction device 200 determining a liver standardized uptake value based on an injected dose of the imaging agent, the plurality of imaging agent activities, and a weight. The image reconstruction device 200 determines a liver standardized uptake value ratio based on the liver standardized uptake value and a blood standard uptake value. Further, the image reconstruction device 200 determines hepatic scores based on the one or more kinetic parameters and the SUVR.

Figure 3:
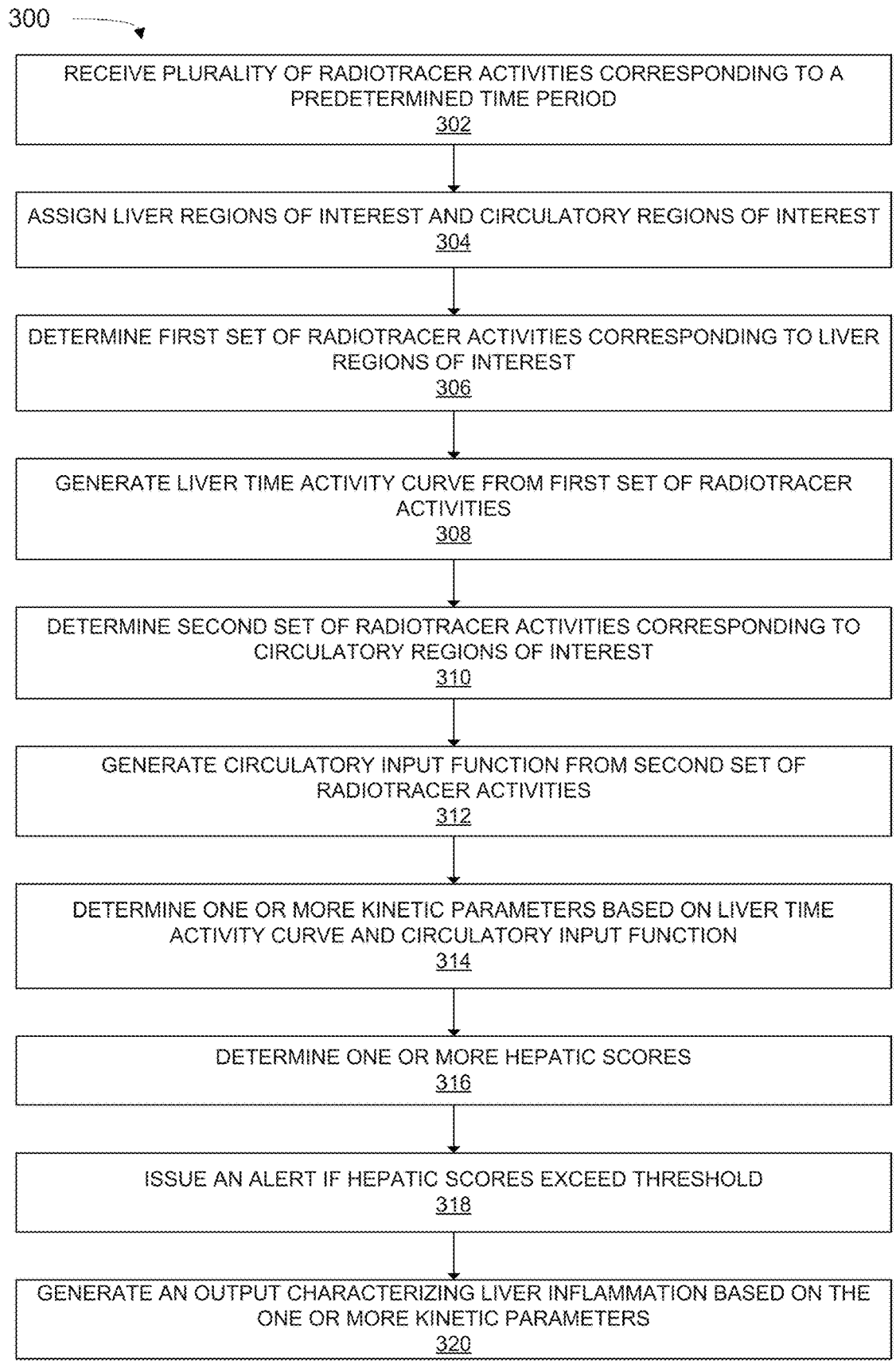
FIG. 3 shows a flow chart of an exemplary method according to some embodiments.

FIG. 3 shows a flowchart 300 of a method for determining kinetic parameters according to embodiments.

In step 302 an image reconstruction device receives a plurality of imaging agent activities corresponding to a predetermined time period. In some embodiments, these imaging agent activities are determined using positron emission tomography (PET). In some embodiments, the image reconstruction device receives these imaging agent activities from a coincidence processing device that is part of a scanning system. In other embodiments, the image reconstruction device receives these imaging agent activities from another device or computer. For example, imaging agent activities may have been scanned and recorded previously and stored on a computer or server database.

The imaging agent activities can correspond to a radiotracer such as FDG that was injected into a patient's body as part of an imaging procedure, such as a PET scan. The time period corresponds to a length of time of the scanning process. For example, if a patient was injected with a dosage of FDG and scanned for a period of one hour, the time period may be one hour. In some embodiments, the scan time may be reduced to less than 10 minutes, or to less than 5 minutes. The time period can comprise a number of time frames. For example, a one hour time period can comprise 60 one minute time frames. The time frames may be different lengths of time. For example, a one hour time period can be separated into 49 time frames, 30 ten second time frames, 10 sixty second time frames, and 9 three-hundred second time frames.

In some embodiments, the plurality of imaging agent activities correspond to or are represented by a set of sinograms or list mode data. In some embodiments, the plurality of imaging agent activities are represented as voxels, and correspond to a time frame of the plurality of time frames and a volume of tissue. For example, a imaging agent activity can correspond to a 5 mm×5 mm×5 mm cube with a given spatial coordinate relative to some reference point and a time frame, such as 00:00→00:30 seconds, the first thirty seconds of the scanning procedure. In some embodiments, the plurality of imaging agent activities are pre-processed before later use. For example, iterative methods such as ordered subset expectation maximization (OSEM) can be used to reconstruct imaging agent activities as PET images.

In step 304, the image reconstruction device can assign liver regions of interest (ROI) and circulatory ROI. In some embodiments, the image reconstruction device may receive ROI and circulatory ROI assigned by a user such as an abdominal radiologist. These ROI define volumes over which statistics can be calculated, for example, the total imaging agent activity or the average imaging agent activity in that region over a given time period. For example, an ROI can be a 25 mm diameter sphere located at some position in the liver.

Figure 4:
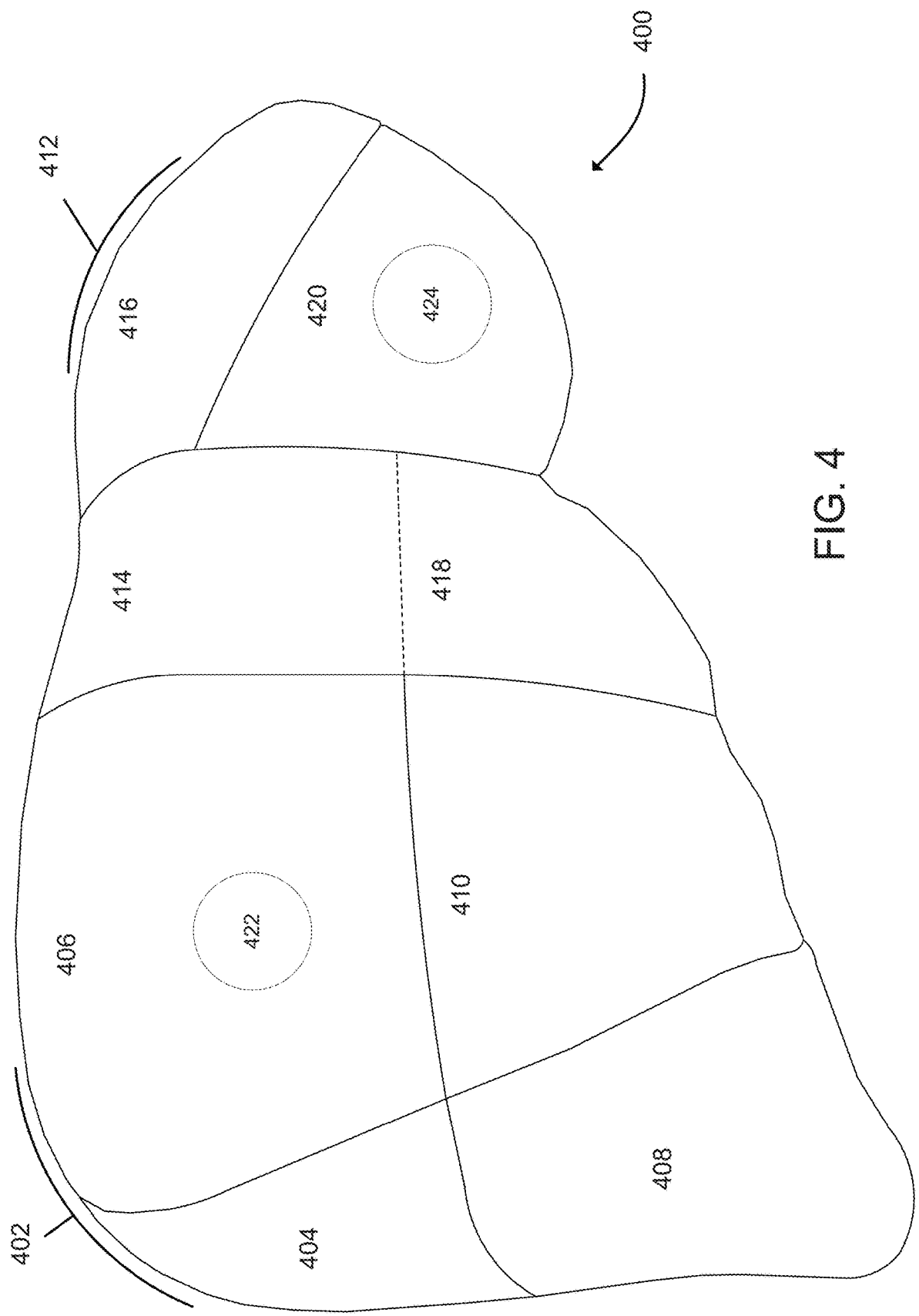
FIG. 4 shows a graphical representation of a liver and liver regions of interest, according to various embodiments.

Regions of interest may be better understood with reference to FIG. 4, which shows a diagram of an anterior view of a liver 400.

The liver 400 comprises a right lobe 402 comprising a right superior posterior subsegment 404, a right superior anterior subsegment 406, a right inferior posterior subsegment 408, and a right inferior anterior subsegment 410. The liver 400 additionally comprises a left lobe 412 comprising a left superior medial subsegment 414, a left superior lateral subsegment 416, a left inferior medial subsegment 418, and a left inferior lateral subsegment 420. Further shown are two liver regions of interest 422 and 424.

The liver ROI 422 and 424 are shown as two spheres on the right superior anterior subsegment 406 and the left inferior lateral subsegment 420. These liver regions of interest correspond to volumes of liver tissue that they encompass. Although only two liver ROI are shown, some embodiments allow for more ROI. For example, liver ROI could be placed on each segment of the liver 404-410 and 414-420. The image reconstruction device can combine or average imaging agent activity in each ROI to produce global liver imaging agent activity, which can in turn be used to generate a liver TAC. For example, an estimate of the average imaging agent activity in the liver can be determined by averaging the imaging agent activity in ROI 424-426.

Circulatory ROI correspond to circulatory tissue that they encompass. The circulatory ROI can capture imaging agent activity in blood flowing through the circulatory system, such as the descending aorta.

Although the regions of interest are shown as spheres, regions of interest can take on any volume. For example, an ROI can be a rectangular prism, cylinder, cone, dodecahedron, pyramid, amorphous voxel array, non-continuous volume distribution, etc.

Returning to FIG. 3, in step 306, the image reconstruction device determines a first set of imaging agent activities corresponding to the liver regions of interest. For example, the first set of imaging agent activities could correspond to imaging agent activities within the liver ROI over a time period.

In step 308, the image reconstruction device generates or determines a liver time activity curve based on the plurality of imaging agent activities. The liver TAC describes imaging agent activity in the liver as a function of time. The liver TAC can be determined in a number of ways, the following is intended only as a non-limiting example.

The image reconstruction device can average the first set of imaging agent activities to determine the liver TAC. As an example, if there are 10 liver regions of interest, each corresponding to 1000 voxels and 100 time frames, the first set of imaging agent activities may corresponds to the 1,000,000 imaging agent activities corresponding to those regions of interest and time frames. The image reconstruction device can average the 10,000 imaging agent activities corresponding to each individual time frame to produce 100 averaged imaging agent activities. Alternatively, the image reconstruction device can perform some other method to combine imaging agent activities. For example, the image reconstruction device can perform a weighted average of imaging agent activities, valuing imaging agent activities from particular regions of interest more than others. Other statistics, such as the total imaging agent activity across all ROI for each time frame could be calculated instead.

In some embodiments, the liver TAC is the collection of averaged or combined imaging agent activities described above. In other embodiments, the liver TAC is a function of time determined based on the averaged imaging agent activities. For example, the image reconstruction device can use an interpolation method, such as linear or spline interpolation to generate a functional representation of the liver TAC.

In step 310, the image reconstruction device determines a second set of imaging agent activities corresponding to one or more circulatory regions of interest. These imaging agent activities correspond to the imaging agent activities in volumes of circulatory tissue encompassed by the one or more circulatory ROI. For example, a circulatory ROI in the descending aorta comprises imaging agent activities measured in the descending aorta over a given time period, and the second set of imaging agent activities can correspond to those imaging agent activities.

In step 312, the image reconstruction device generates or determines a circulatory input function based on the plurality of imaging agent activities. The circulatory input function corresponds to the imaging agent activity contribution to the liver by the circulatory system. Similar to the liver TAC, the circulatory input function can be determined through the use of ROI. The circulatory input function can be determined in a number of ways, the following is intended only as a non-limiting example.

The image reconstruction device can average imaging agent activities from the second set of imaging agent activities. As an example, if there is one circulatory ROI corresponding to 1000 voxels and 100 time frames, the second set of imaging agent activities can correspond to the 100,000 circulatory imaging agent activities corresponding to that ROI and those time frames. The image reconstruction device can average the 1000 imaging agent activities corresponding to each individual time frame to produce 100 averaged circulatory imaging agent activities.

In some embodiments, the image reconstruction device generates a circulatory input function from the averaged imaging agent activities as described above. The circulatory input function can be generated in substantially the same way as the liver TAC. In some embodiments, the circulatory input function is represented by the averaged imaging agent activities. In other embodiments, the circulatory input function is a continuous or near continuous function of time, and is determined using interpolation, curve fitting, or any other appropriate method.

In step 314, the image reconstruction device determines one or more kinetic parameters corresponding to a kinetic model of a imaging agent in the liver based on the liver TAC and circulatory input function. Step 314 may be better understood with reference to FIG. 5.

Figure 5:
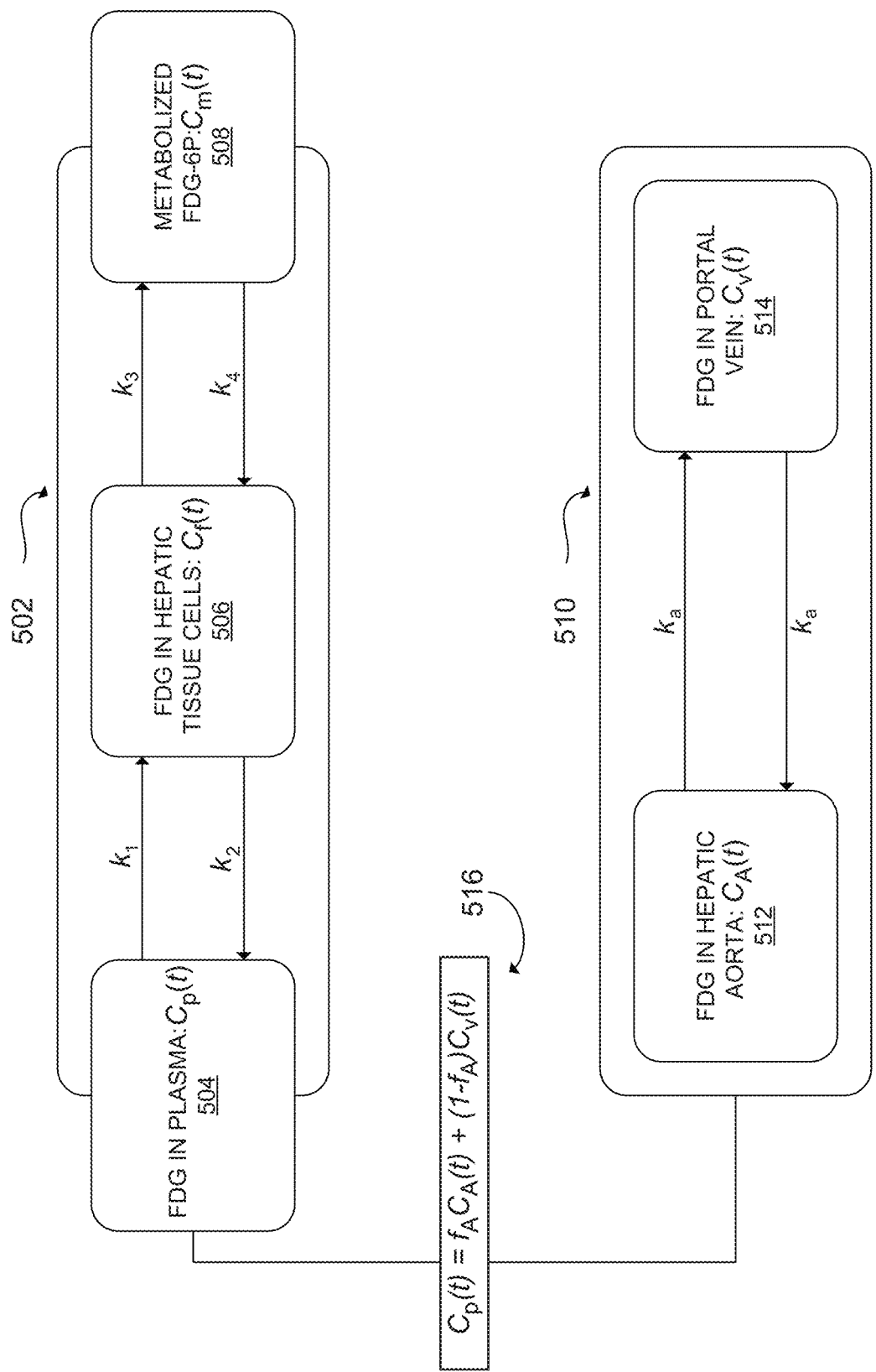
FIG. 5 shows a three-compartment model and a dual blood input model of the liver, according to various embodiments.

FIG. 5 shows an exemplary kinetic model of FDG in a liver. The kinetic model of a radiotracer in the liver describes the movement and quantity of the radiotracer in the liver. A kinetic model can be a compartment model, where locations or states of the radiotracer are represented by different compartments. The kinetic model of FDG in the liver can be a three-compartment model 502 comprising an FDG in plasma compartment 504, an FDG in hepatic tissue cells compartment 506, and a metabolized FDG-6P compartment 508. FIG. 5 also shows a dual blood input model 510 comprising an FDG in hepatic artery compartment 512 and an FDG in portal vein compartment 514. Additionally, FIG. 5 shows an equation 516 relating the FDG in plasma compartment 504 to the dual blood input model 510. Further, FIG. 5 shows five kinetic parameters, $K_1$, $k_2$, $k_3$, $k_4$, $k_a$, and $f_A$.

The FDG in plasma compartment 504 describes the radiotracer activities of FDG in the patient's bloodstream. These radiotracer activities are represented by a function Cp(t) that describes the radiotracer activity in the compartment as a function of time. As FDG circulates through the patient's bloodstream, some FDG is transported into hepatic tissue cells. The rate at which FDG moves from the FDG in plasma compartment 504 to the FDG in hepatic tissue cells compartment 506 is the first kinetic parameter K1. FDG can also diffuse or be transported out of hepatic tissue cells into the blood stream. The rate at which FDG moves from the FDG in hepatic tissue cells compartment 506 to the FDG in plasma compartment 504 is the second kinetic parameter k2.

The FDG in plasma compartment 504 is further modelled by a dual blood input model 510. The liver receives blood via the hepatic artery proper and the portal vein. As such, the dual blood input model is comprised of two compartments, an FDG in hepatic aorta compartment, described by a radiotracer activity function CA(t) and a FDG in portal vein compartment, described by a radiotracer activity function Cv(t). The relationship between CA(t), Cv(t) and Cp(t) is described by equation 516. fA, the hepatic artery fraction, describes the proportion of blood that is delivered to the liver via the hepatic artery, and (1−fA) describes the remaining proportion.

Blood entering the liver via the proper hepatic artery flows from the common hepatic artery, which in turn flows from the celiac artery, which further in turn flows from the abdominal aorta. By contrast, blood entering the liver via the portal vein has first travelled through the gastrointestinal system and arrives via the confluence of the superior mesenteric and splenic veins. As a result, some FDG is dispersed before it arrives at the liver via the portal vein. This dispersal is related to a rate kinetic parameter $k_a$, which describes the rate at which FDG in the portal vein flows through the gastrointestinal system before entering the liver. The portal vein input function $C_v(t)$ can be described as a dispersed version of the aortic input function $C_A(t)$:

$$C_v(t) = k_a \exp(-k_a t) \otimes C_A(t) \qquad \text{Eq. 1}$$

The second compartment of the three-compartment model is the FDG in hepatic tissue cells compartment 506. This compartment describes FDG that is in hepatic tissue cells. The radiotracer activities corresponding to radiotracers in this compartment is described by the function Cf(t). As stated above, FDG can be transported or diffuse out of the hepatic tissue cells at a rate k2. FDG can also be phosphorylated into FDG-6P in the hepatic tissue cells. While the FDG is not leaving the hepatic tissue cells, the FDG-6P has its own compartment, and the phosphorylation is regarded as an outflow from the FDG in hepatic tissue compartment 506 to the metabolized FDG-6P compartment 508. The rate at which FDG is phosphorylated by hepatic tissue cells to FDG-6P is the kinetic parameter k3. FDG-6P can also be dephosphorylated into FDG. This is described by the kinetic model as a movement from the metabolized FDG-6P compartment 508 to the FDG in hepatic tissue cells compartment 606. The rate at which FDG-6P is dephosphorylated into FDG is the kinetic parameter k4.

The third compartment of the three-compartment model is the metabolized FDG-6P compartment 508. The radiotracer activity in this compartment is described by the function Cm(t). The rate of radiotracer movement in and out of this compartment is described by the kinetic parameters k3 and k4 respectively, as described above.

The change in radiotracer activity in a compartment as a function of time is proportional to the radiotracer activity in that compartment, the radiotracer activity in adjacent compartments, and the kinetic parameters described above. For example, the change in radiotracer activity in the metabolized FDG-6P compartment 608 is a function of the radiotracer activity $C_m(t)$, the radiotracer activity $C_f(t)$, and kinetic parameters $k_3$ and $k_4$. Expressed as an equation:

$$\frac{d}{dt}C_m(t) = k_3 C_f(t) - k_4 C_m(t) \qquad \text{Eq. 2}$$

In effect, the change in radiotracer activity is proportional to the amount entering the compartment from adjacent compartments, and the amount leaving the compartment itself.

In this way, a system of differential equations can be defined relating the change in radiotracer activities:

$$\frac{d}{dt}c(t) = Ac(t) + bC_A(t) \qquad \text{Eq. 3}$$

Where:

$$c(t) = \begin{bmatrix} C_f(t) \\ C_m(t) \\ C_V(t) \end{bmatrix}, A = \begin{bmatrix} -(k_2+k_3) & k_4 & K_1(1-f_A) \\ k_3 & -k_4 & 0 \\ 0 & 0 & k_a \end{bmatrix}, b = \begin{bmatrix} K_1 f_A \\ 0 \\ k_a \end{bmatrix} \qquad \text{Eq. 4}$$

The total radiotracer activity $C_T(t; \theta)$ measured by a PET scan is the sum of the radiotracer activity of different compartments, multiplied by the fractional blood volume $v_b$, a kinetic parameter describing the proportion of the volume of blood in the liver:

$$C_T(t;\theta) = (1-v_b)[C_f(t)+C_m(t)]+v_b[(1-f_A)C_v(t)+f_A C_A(t)] \qquad \text{Eq. 5}$$

Where $\theta = [v_b, K_1, k_2, k_3, k_4, k_a, f_A]^T$, a vector collecting all kinetic parameters.

In some embodiments, the aortic input function $C_A(t)$ is the "circulatory input function" determined using circulatory regions of interest, as described above. In some embodiments, the circulatory input function (i.e., the aortic input function) corresponds to radiotracer activities from a circulatory region of interest, for example, in the descending aorta for each time frame of a plurality of time frames. The portal vein input function can be determined using the aortic input function using the dispersion equation described above.

The image reconstruction device can determine the kinetic parameters from the above equations using any appropriate mathematical analysis. For example, joint estimation of kinetic parameters using the model equation and non-linear least squares estimation:

$$\hat{\theta} = \operatorname*{argmin}_{\theta} WRSS(\theta), \; WRSS(\theta) = \sum_{m=1}^{M} w_m \left[ \check{c}_m - C_T(t_m; \theta) \right]^2 \qquad \text{Eq. 6}$$

Where the estimate of parameters $\hat{\theta}$ are the parameters that minimize the weighted residual sum of squares function WRSS($\theta$), and $\check{c}_m$ is the radiotracer activity of the liver TAC at timeframe m. The Levenberg-Marquardt method, or another suitable iterative method can be used to solve the optimization problem. In some embodiments, the image reconstruction device initially estimates the kinetic parameters before they are determined using the above method.

A method according to some embodiments additionally comprises the image reconstruction device determining a liver standardized uptake value based on an injected dose of the radiotracer, the plurality of radiotracer activities, and a weight.

The liver standardized uptake value is a ratio of the radiotracer activity in the liver to the total injected dose distributed over the patient's entire body (represented by the weight). The injected dose of the radiotracer is the known radiotracer activity or radioactive dose. For example, a patient may be injected with a dose of 10 mCi FDG. There are a number of methods that the image reconstruction device can use to determine the radiotracer activity in the liver. For example, radiotracer activities from multiple liver ROI could be averaged to determine an average radiotracer activity per unit volume. This average radiotracer activity can be multiplied by the total volume of the liver in order to estimate the radiotracer activity of the liver.

The image reconstruction device can determine the liver standardized uptake value by first dividing the injected dose by the weight, then determining the radiotracer activity in the liver based on the plurality of radiotracer activities, and then dividing the radiotracer activity in the liver by the injected dose per unit weight.

A method according to some embodiments additionally comprises the image reconstruction device determining a liver standardized uptake value ratio based on the liver standardized uptake value and a blood standardized uptake value. The liver standardized uptake value ratio is a ratio of the liver standardized uptake value to the blood standardized uptake value. The blood SUV can be determined in a similar way as the liver SUV, e.g., using regions of interest to characterize radiotracer activity in the blood, determining the radio of injected radiotracer dose to weight, and determining the blood SUV as the blood radiotracer activity divided by the radiotracer dose per unit weight.

Returning to FIG. 3, in step 316, the image reconstruction device determines one or more hepatic scores based on one or more kinetic parameters and the liver SUVR. The image reconstruction device can use one or more of the kinetic parameters as inputs to a hepatic scoring function. In some embodiments, the image reconstruction device determines a hepatic inflammation score based only on the kinetic parameter $K_1$. For example, the hepatic inflammation score $H_1$ could be calculated according to the following equation: $H_1=9-6.7*K_1$. In this example, a $K_1$ of 1.33 would result in a hepatic inflammation score of 1, and a $K_1$ equal to 0.6 would result in a hepatic inflammation score of 5.

The image reconstruction device can use different kinetic parameters or combinations of kinetic parameters to determine a hepatic inflammation score as well. For example, the image reconstruction device can determine a weighted average of the kinetic parameters and determine the hepatic inflammation score based on that weighted average.

In some embodiments, the image reconstruction device also determines a hepatic steatosis score based on the liver standardized uptake value ratio. For example, the hepatic steatosis score $H_S$ can be a function of the liver SUVR, such as $H_S=14-10*SUVR$. In this non-limiting example, a liver SUVR of 1.3 corresponds to a hepatic steatosis score of 1, and a liver SUVR of 1.1 corresponds to a hepatic steatosis score of 3.

In some embodiments, the image reconstruction device determines a hepatic fibrosis score HF based on the liver standardized uptake value ratio and at least one kinetic parameter of the one or more kinetic parameters. For example, the hepatic fibrosis score can be determined based on a ratio of $K_1$ to the SUVR.

In step 318, the image reconstruction device compares the hepatic scores against threshold hepatic scores and issue an alert if the any one or more of the hepatic scores exceeds corresponding threshold scores. The alert can comprise a visual alert, such as a warning appearing on a display, such as the display 204 of image reconstruction device 200 from FIG. 2. The alert can also comprise audio, such as a chime, tone, or recorded message. Further, the alert can comprise an electronic message sent to another computer or device, such as an email message sent to a doctor's email account or a message sent to a server computer. The alert can include relevant information about the hepatic scores, such as the hepatic score itself and patient statistics (e.g., age, weight, height, etc.) the alert can also comprise the one or more kinetic parameters.

At step 320, the image reconstruction device may generate an output characterizing liver inflammation in the liver based on the one or more kinetic parameters. For example the image reconstruction device may generate an output indicating the presence (or absence) of nonalcoholic fatty liver disease (NAFLD) and/or nonalcoholic steatohepatitis (NASH) in the liver. The output may be generated in view of the hepatic scores determined at step 316. In some embodiments, the image reconstruction device may generate an output characterizing liver inflammation in the liver based on the one or more kinetic parameters without having to determine or prior to determining the hepatic scores.

Steps 304-314 generally describe steps for determining kinetic parameters using ROI. As described above ROI are defined for both the liver and the circulatory system and used by the image reconstruction device to generate a liver TAC and circulatory input function respectively. The liver TAC and circulatory input function are used by the image reconstruction device to determine one or more kinetic parameters as described above. However, some embodiments provide for an alternative method of determining kinetic parameters using parametric imaging methods. These methods will be described below.

As noted above, the image reconstruction device receives a plurality of imaging agent activities corresponding to a predetermined time period. These imaging agent activities correspond to imaging agent activity in a patient's body both spatially and temporally, such that each imaging agent activity corresponds to a specific volume of tissue and a time frame during which the imaging agent activity was observed. These volumes of tissue can be represented by voxels as described above, and multiple imaging agent activities, corresponding to different time frames, can correspond to each voxel.

As an alternative to the methods described above, the image reconstruction device can determine a plurality of liver TACs, each liver TAC corresponding to a voxel, rather than generating a single liver TAC for the entire liver. The liver TAC for each voxel can be represented as a sequential vector of imaging agent activities corresponding to that voxel. For example, if a sixty minute scanning procedure was split up into 60 one minute time frames, the liver TAC for a given voxel can be represented as imaging agent activities recorded within that volume of tissue during each one minute time frame of the 60 minute scanning procedure. Alternatively, the liver TAC for each voxel can be a imaging agent activity function of time determined based on the corresponding voxel imaging agent activities using any suitable method of curve fitting, interpolation, etc., as described above.

Rather than determining a single set of kinetic parameters $\theta=[v_b, K_1, k_2, k_3, k_4, k_a, f_A]^T$, the image reconstruction device can determine kinetic parameters for each voxel of imaging agent activity data. The image reconstruction device can determine the kinetic parameters for each voxel using similar methods to the method above, instead performing joint parametric estimation for each liver TAC of the plurality of liver TAC rather than performing joint parametric estimation using a single liver TAC.

In doing so, the image reconstruction device can generate a parametric map of the kinetic parameters, a collection of voxels each corresponding to a set of kinetic parameters. The image reconstruction device can produce a single set of kinetic parameters from the parametric map using any number of suitable methods.

As a first example, liver ROI can be assigned by the image reconstruction device or an abdominal radiologist to the parametric map. Rather than averaging imaging agent activities in liver ROI as described above, the image reconstruction device can average kinetic parameters in liver ROI for the parametric map to produce a single set of kinetic parameters associated with a kinetic model of a imaging agent in the liver. The single set of kinetic parameters can be used by the image reconstruction device to determine one or more hepatic scores, as described above in reference to step 316.

As a further alternative, the image reconstruction device can determine one or more hepatic score corresponding to each voxel using the kinetic parameters corresponding to those voxels to produce a hepatic score map. The image reconstruction device or an abdominal radiologist could assign liver ROI to the hepatic score map and average the hepatic scores across the liver ROI to produce a single set of hepatic scores corresponding to the entire liver.

The methods described herein can be employed on any animal, e.g., a human. In some embodiments, the human is suspected of having a liver disorder or having at least one indicator of a liver disorder before being submitted to a dynamic PET method as described herein. Exemplary liver disorder indicators can include, but are not limited to, having a liver biopsy, fatty liver detected by ultrasound, patient high BMI score, having one or more risk factors for diabetes, and/or elevated liver enzyme levels (e.g., alanine transaminase (ALT) or aspartate transaminase (AST)).

Any of the computer systems mentioned herein may utilize any suitable number of subsystems. In some embodiments, a computer system includes a single computer apparatus, where the subsystems can be components of the computer apparatus. In other embodiments, a computer system can include multiple computer apparatuses, each being a subsystem, with internal components.

A computer system can include a plurality of the components or subsystems, e.g., connected together by external interface or by an internal interface. In some embodiments, computer systems, subsystems, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g., an application specific integrated circuit or field programmable gate array) and/or using computer software with a generally programmable processor in a modular or integrated manner. As used herein a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer or other suitable display for providing any of the results mentioned herein to a user.

Any of the methods described herein may be totally or partially performed with a computer system including one or more processors, which can be configured to perform the steps. Thus, embodiments can be involve computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, and of the steps of any of the methods can be performed with modules, circuits, or other means for performing these steps.

The specific details of particular embodiments may be combined in any suitable manner without departing from the spirit and scope of embodiments of the invention. However, other embodiments of the invention may be involve specific embodiments relating to each individual aspect, or specific combinations of these individual aspects. The above description of exemplary embodiments of the invention has been presented for the purpose of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications and description mentioned herein are incorporated by reference in their entirety for all purposes. None is admitted to be prior art.

Embodiments may be better understood with reference to the following examples directed at patient studies for diagnosing NAFLD or NASH using the analysis method described herein.

EXAMPLE 1

Patient Characteristics

Fourteen patients with NAFLD were included in the first patient study. These patients had a liver biopsy as a part of routine clinical care or for enrollment in clinical trials. Patients with history of alcohol abuse, chronic hepatitis B or C, or other chronic liver disease other than NAFLD were excluded from the first patient study.

Liver Histopathology

Liver biopsies were performed under ultrasound guidance and scored according to the nonalcoholic steatohepatitis clinical research network (NASH-CRN) criteria. The NAFLD activity score (NAS, range 0-8) is comprised of severity of steatosis, inflammation, and hepatocellular ballooning. While a NAS score greater than 4 has been reported to correlate with the presence of NASH, the scores of lobular inflammation and ballooning degeneration are noted to represent hepatic inflammation and injury, and are therefore combined to create an overall "hepatic inflammation" score (range 0-5). In the first patient study, an inflammation score>3 was considered indicative of high inflammation, and a score<3 and score=3 were deemed as low and medium inflammation, respectively.

Dynamic $^{18}$F-FDG PET/CT

Scan Protocol: Dynamic $^{18}$F-FDG PET studies were performed with the GE Discovery 690 PET/CT scanner. Diabetic patients were instructed to hold their long-acting insulin dose after midnight and morning dose of short acting insulin. Each patient was injected with 10 mCi $^{18}$F-FDG. List-mode time-of-flight data acquisition started right after the intravenous bolus administration and lasted for one hour. At the end of PET scan, a low-dose CT scan was performed for attenuation correction for PET. Dynamic PET data were binned into 49 time frames using the sampling schedule: 30×10 s, 10×60 s, and 9×300 s. Dynamic PET images were then reconstructed using a software with the standard ordered subsets expectation maximization (OSEM) algorithm with 2 iterations and 32 subsets.

Extraction of Blood and Tissue Time Activity Curves (TACs): Eight spherical regions of interest (ROI), each with 25 mm in diameter, were placed on the eight segments of the liver avoiding any major blood vessels. These ROI placements were tuned and confirmed by an abdominal radiologist. The averaged FDG activity in all 8 ROIs was extracted from the dynamic images to form a global liver TAC. An additional ROI is placed in the descending aorta region to extract image-derived aortic input function.

Dual-Input Kinetic Modeling

Figure 6:
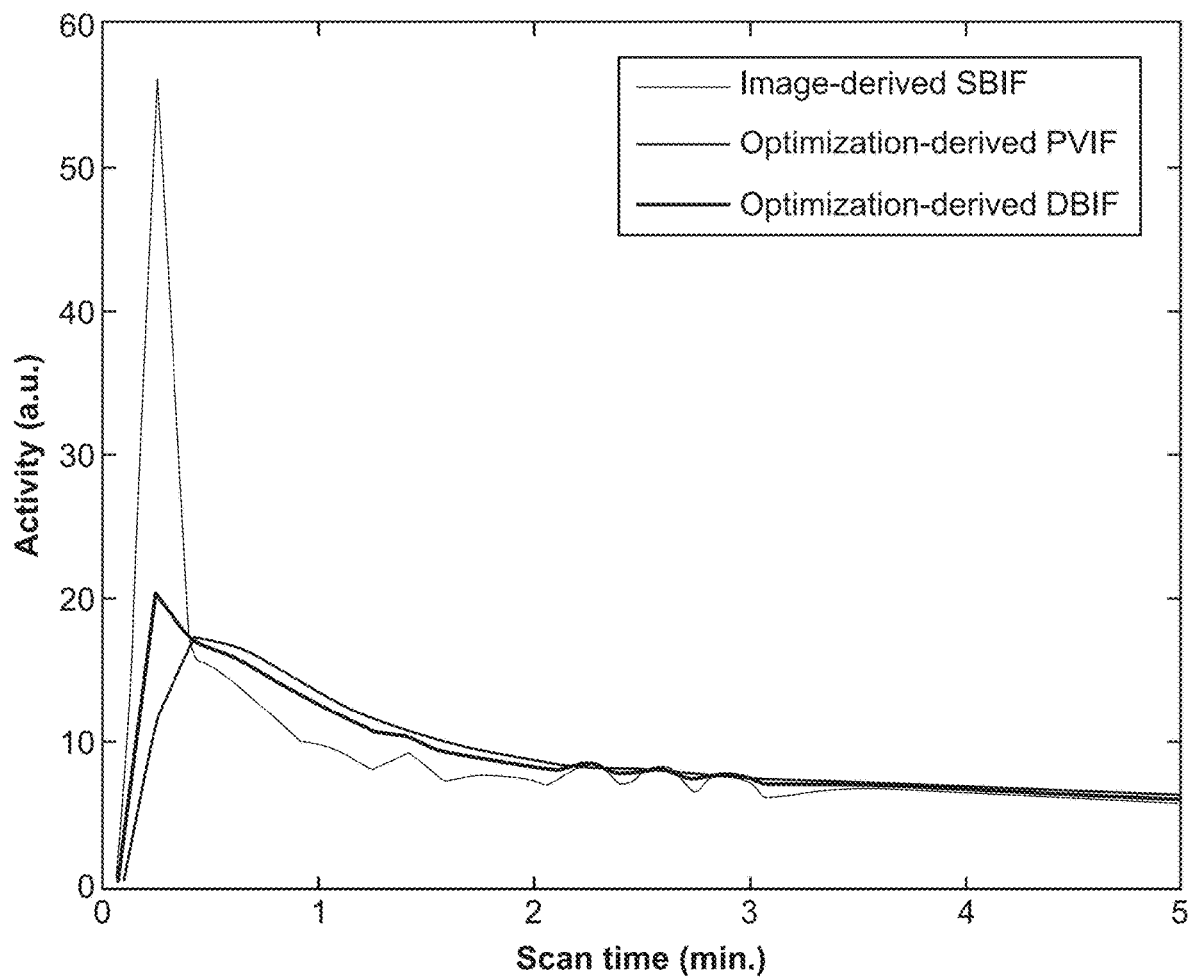
FIG. 6 shows an example of an optimization-derived dual blood input function and its components from hepatic artery and portal vein: image-derived single blood input function and portal vein input function (PVIF), according to various embodiments.

Compartmental Model with dual-blood input function (DBIF): FDG kinetics commonly follow the two-tissue compartmental model as shown in FIG. 5. Glucose transporters transport $^{18}$F-FDG from blood to hepatic tissue with the rate constant $K_1$ (mL/min/mL) and from hepatic tissue to blood with the rate $k_2$ (1/min). FDG is phosphorylated by hexokinase in cells into FDG 6-phosphate with the rate $k_3$ (1/min) and the dephosphorylation process occurs with the rate $k_4$ (1/min). $C_p(t)$, $C_f(t)$ and $C_m(t)$ represent the FDG concentration in the plasma compartment, free-state FDG in the hepatic tissue compartment, and metabolized FDG 6-phosphate in the tissue, respectively. In traditional kinetic modeling with single-blood input function (SBIF), only blood supply from the aorta is considered and thus the input function $C_p(t)$ is equivalent to the aortic input function $C_A(t)$. To account for the effect of dual blood supplies in the liver, a flow-weighted sum of the aortic input $C_A(t)$ and portal vein input $C_V(t)$ can be used to model the dual-blood input function (DBIF):

$$C_p(t)=(1-f_A)C_V(t)+f_A C_A(t) \qquad \text{Eq. 7}$$

where $f_A$ is the fraction of hepatic artery contributing to the overall liver blood flow. As shown in FIG. 6 portal vein can be considered as an additional compartment given FDG in portal vein flows through the gastrointestinal system with the rate $k_a$ (1/min) before entering into the liver. Thus, the portal vein input function $C_V(t)$ follows an analytical solution $$C_V(t)=k_a \exp(-k_a t) \otimes C_A(t), \qquad \text{Eq. 1}$$

which represents a dispersed version of the aortic input function $C_A(t)$. As a result, the combined compartmental model is equivalently described by a set of differential equations:

$$\frac{d}{dt}c(t) = Ac(t) + bC_A(t), \qquad \text{Eq. 3}$$

Where $$c(t) = \begin{bmatrix} C_f(t) \\ C_m(t) \\ C_V(t) \end{bmatrix}, A = \begin{bmatrix} -(k_2+k_3) & k_4 & K_1(1-f_A) \\ k_3 & -k_4 & 0 \\ 0 & 0 & k_a \end{bmatrix}, b = \begin{bmatrix} K_1 f_A \\ 0 \\ k_a \end{bmatrix}. \qquad \text{Eq. 4}$$

The total activity that can be measured by PET is the sum of different compartments:

$$C_T(t;\theta)=(1-v_b)[C_f(t)+C_m(t)]+v_b[(1-f_A)C_V(t)+f_A C_A(t)], \qquad \text{Eq. 5}$$

where $v_b$ is the fractional blood volume and $\theta=[v_b, K_1, k_2, k_3, k_4, k_a, f_A]^T$ is a vector collecting all unknown parameters.

Joint Estimation of Kinetic and Input Parameters: All model parameters are jointly estimated by fitting a measured liver TAC č using the model equation and following nonlinear least square estimation:

$$\hat{\theta} = \arg\min_\theta WRSS(\theta), \; WRSS(\theta) = \sum_{m=1}^{M} w_m [\check{c}_m - C_T(t_m;\theta)]^2. \qquad \text{Eq. 6}$$

where $WRSS(\theta)$ denotes the weighted residual sum of squares of the curve fitting and $w_m$ denotes the weighting factor for time frame m. It would become equivalent to the population-based DBIF if the parameters $f_A$ and $k_a$ are assigned with fixed population means (if known). Based on the initial analysis of the patient data sets, the initials of kinetic parameters are set to $v_b$=0.01, $K_1$=1.0, $k_2$=1.0, $k_3$=0.01, $k_4$=0.01, $k_a$=1.0, $f_A$=0.01.

Comparison of Kinetic Models

The following three input models are compared: traditional model with SBIF, model with population-based DBIF and model with optimization-derived DBIF. In the first patient study, the SBIF was derived from the descending aorta region in dynamic FDG-PET images. To utilize reported population means for the population-based DBIF, the following portal vein input model is used:

$$C_v(t) = (\bar{\beta}/(\bar{\beta}+t)^2) \otimes C_A(t), \quad \text{Eq. 8}$$

The portal vein input model is very similar to the exponential-based model in Eq. 1 but not easily integrated into the differential equations for joint estimation. $\bar{\beta}$=0.5 and $f_A$=0.25 were previously reported for FDG.

Comparison Using Statistical Criteria: The three models were compared using two predetermined statistical criteria for model selection for TACs: corrected Akaike information criterion (AIC) and F test. The AIC is defined by $$AIC = -M\ln\left(\frac{WRSS}{M}\right) + 2n + \frac{2n(n+1)}{M-n-1}, \quad \text{Eq. 9}$$

where n denotes the total number of unknown parameters, where n=5 for the SBIF and population-based DBIF models and n=7 for the optimization-derived DBIF model. Here AIC was corrected for finite sample sizes due to the ratio $$\frac{M}{n} \leq 40.$$

A lower AIL value indicates a better selection of model.

The F test compares a complex model 2 with a simple model 1 using $$F = \frac{(WRSS_2 - WRSS_1)/(n_2 - n_1)}{WRSS_2/(M - n_2)}, \quad \text{Eq. 10}$$

where the degree of freedom (number of unknown parameters) $n_2 > n_1$. A larger F value indicates better fit. If the p value of F test is 0.05 or less, the model 2 is then considered significantly better than model 1.

Evaluation Using Histopathological Inflammation Data: Patients in the first patient study were divided into three groups according to their histopathological inflammation scores: low inflammation (<3), medium inflammation (=3), and high inflammation (>3). To examine the capability of FDG kinetic parameters for differentiating different inflammation groups, a two-sample 2-sided t-test at the 0.05 level was used to test the difference of group means and the Mann-Whitney U test was used to test difference of group medians. P-values less than 0.05 were considered as statistically significant in the first patient study.

Results

Patient Characteristics

Majority of the patients were white (75%) while 25% were Hispanics. Female patients formed 67% of the cohort with 75% of the patients between the ages 40-70 years and 25% between 18-39 years. The mean BMI was 34±6 kg/m².

The mean fasting glucose prior to PET scan was 115±33 mg/dL. The patient population had an equitable spread across NAS score (≥5 of 58%). Two thirds of patients had hepatic inflammation sore of ≥3.

Demonstration of Dual-Blood Input Function

FIG. 6 demonstrates an optimization-derived DBIF from a patient data set. Only the first 5 minutes are shown in the figure and the curves after 5 minutes are very similar among others. The DBIF is a weighted combination of the image-derived SBIF and the portal vein input function derived from the optimization. In this example, the weighting factor $f_A$ was 0.19. The DBIF has a much lower peak value than the SBIF because the contribution from hepatic artery is small (19%) while the contribution from portal vein is great (81%).

Evaluation of TAC Fit Quality

Figure 7A:
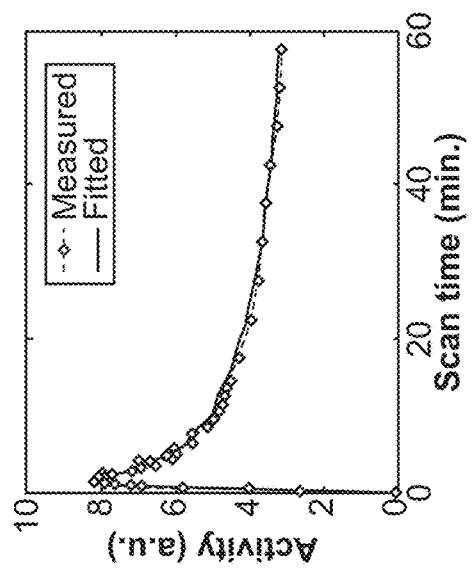
FIG. 7A shows a fit of a liver time activity curve using a single blood input function, according to various embodiments.
Figure 7B:
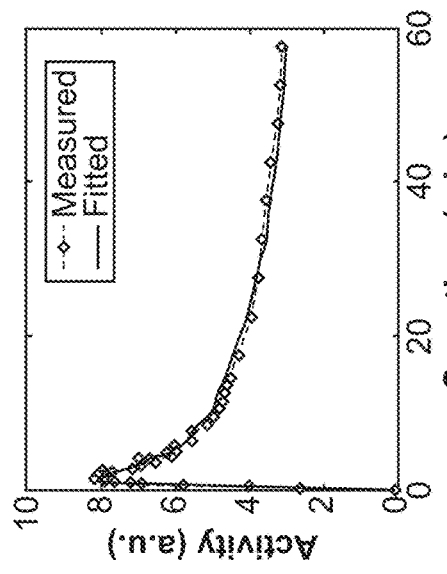
FIG. 7B shows a fit of a liver time activity curve using a population-based dual blood input function, according to various embodiments.
Figure 7C:
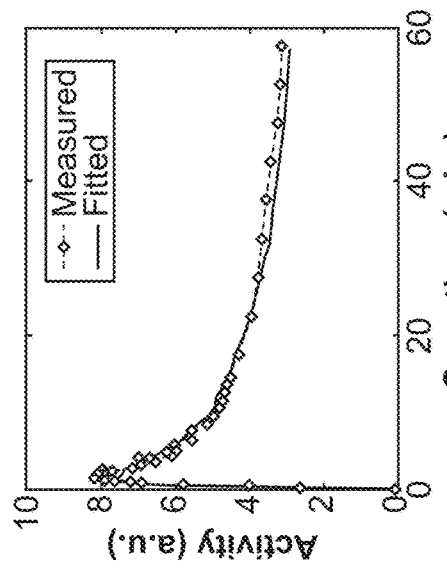
FIG. 7C shows a fit of a liver time activity curve using an optimization-derived dual blood input function, according to various embodiments.
Figure 7D:
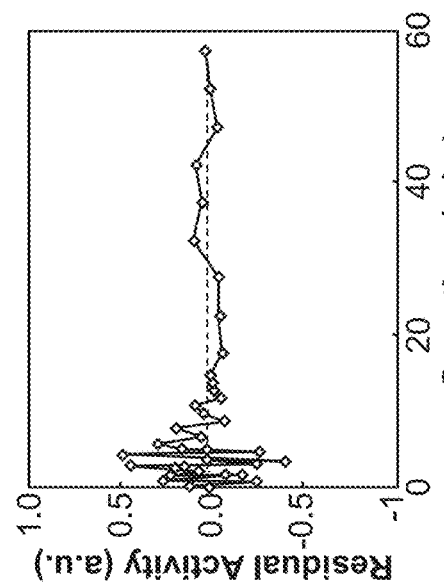
FIG. 7D shows residuals corresponding to the fit of a liver time activity curve using a single blood input function, according to various embodiments.
Figure 7E:
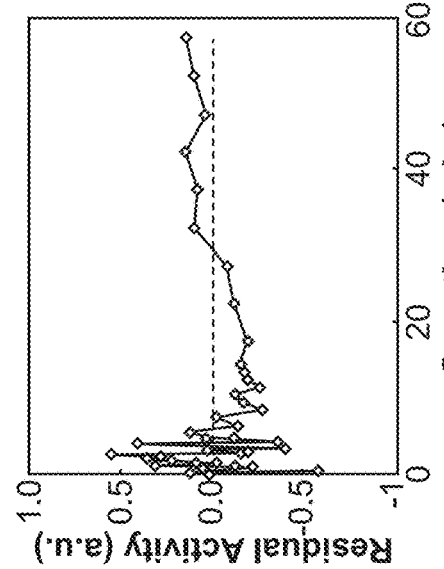
FIG. 7E shows residuals corresponding to the fit of a liver time activity curve using a population-based dual blood input function, according to various embodiments.
Figure 7F:
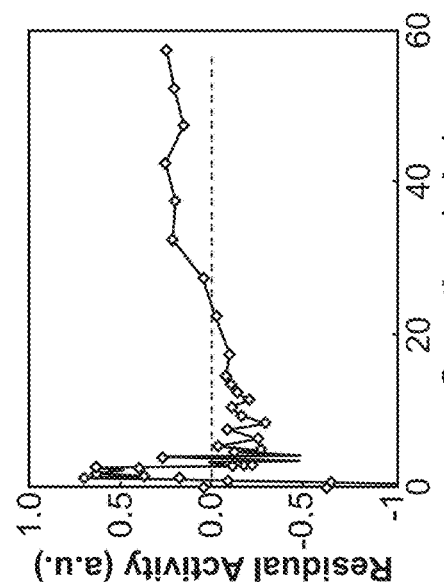
FIG. 7F shows residuals corresponding to the fit of a liver time activity curve using an optimization-derived dual blood input function, according to various embodiments.

FIGS. 7A-7C show the fittings of the liver TAC using the image-derived SBIF, population-based DBIF and optimization-derived DBIF. The residual plots of these fits are shown in FIGS. 7D-7F. The fitting with SBIF couldn't fit the early-time peak and late time points due to lack of the portal vein component in the input function. The population-based DBIF provided an improved fit of the peak but still suffered error for late time points due to inaccuracy of the population means for a specific patient data set. A linear trend was observed in the residual plots (FIGS. 7D and 7E) for these two approaches, indicating a systematic bias in the fitting. The optimization-derived DBIF estimated the input parameters from the data and fit both the peak at early time and late time points closely. The linear trend was removed and the residuals became asymptotically normal.

Figure 8:
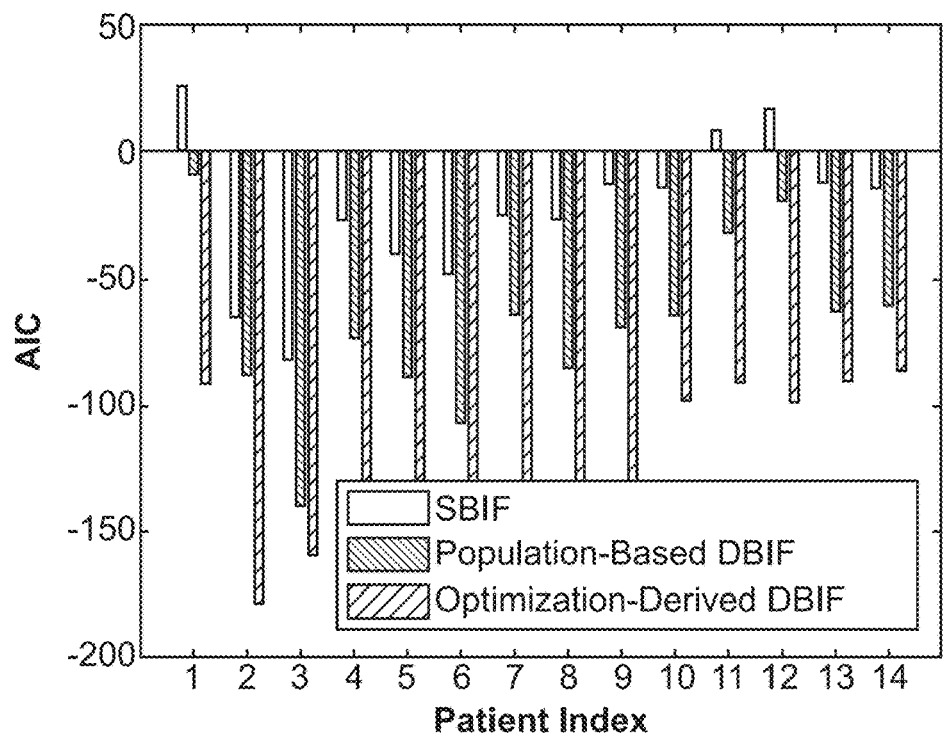
FIG. 8 shows Akaike information criterion values of a liver time activity curve fitting with different input function models, according to various embodiments.

The AIC values of the three fittings were −81, −140 and −159, respectively. AIC values of the three input models are further compared in FIG. 8 for all individual patients in the cohort. The average AIC was −23±30 by SBIF, −69±34 by the population-based DBIF, and −128±34 by the optimization-derived DBIF. The optimization-derived DBIF model had the lowest AIC in all patients.

The results of F test are given in Table 1. The minimum F value among different patients was 80.5 for comparing the optimization-derived DBIF with SBIF and 13.4 for comparing the optimization-derived DBIF with population-based DBIF model, both greater than the F critical value 3.2 calculated with $n_1$=5 and $n_2$=7 for a p value of 0.05. The p values of F test in individual patients are all small (<0.0001), indicating the optimization-derived DBIF is more appropriate for TAC fitting than the traditional SBIF and population-based DBIF models.

TABLE 1

F statistics of model comparison (F critical value is 3.2 at the significance level of 0.05)

| Model Comparison | F Values Mean ± SD | Min | max | P Values |
|---|---|---|---|---|
| Optimization-Derived DBIF vs SBIF | 200.2 ± 102.7 | 80.5 | 389.9 | <0.0001 |
| Optimization-Derived DBIF vs Population-Based DBIF | 67.5 ± 43.7 | 13.4 | 137.7 | <0.0001 |

TABLE 2

Mean and standard deviation of FDG kinetic parameters estimated by different input function approaches

|  | $K_1$ | $k_2$ | $k_3$ | $k_4$ | $K_i$ |
|---|---|---|---|---|---|
| SBIF | 0.5112 ± 0.2064 | 0.4983 ± 0.1760 | 0.0008 ± 0.0010 | 0.0512 ± 0.0465 | 0.0008 ± 0.0010 |
| Population-Based DBIF | 0.9787 ± 0.5509 | 0.9197 ± 0.4222 | 0.0011 ± 0.0011 | 0.0196 ± 0.0291 | 0.0010 ± 0.0011 |
| Optimization-Derived DBIF | 0.9829 ± 0.2730 | 1.1053 ± 0.2488 | 0.0141 ± 0.0070 | 0.0534 ± 0.0263 | 0.0119 ± 0.0051 |

Change in Kinetic Parameters

Figure 9:
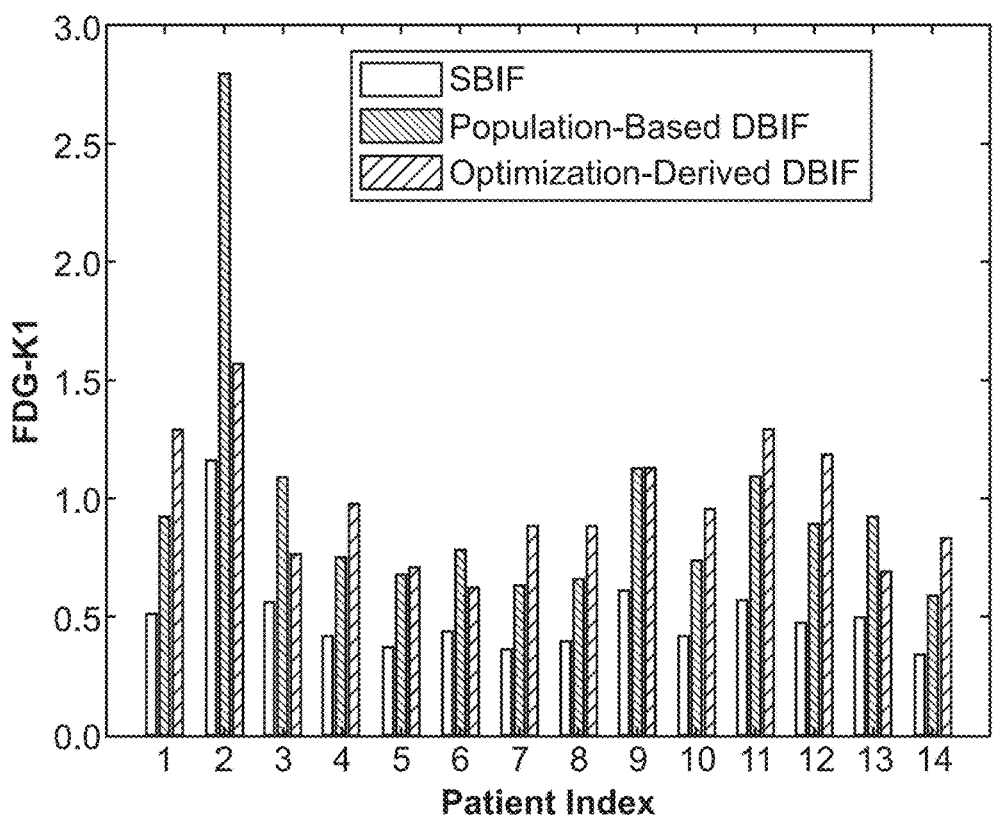
FIG. 9 shows FDG K1 values estimated by different input function models, according to various embodiments.

The three input models resulted in different estimates in kinetic parameters. The mean and standard deviation of kinetic parameters $K_1$, $k_2$, $k_3$, $k_4$ and $K_i = K_1 k_3/(k_2+k_3)$ estimated by the three approaches are listed in Table 2. A reversible kinetic model (i.e., $k_4 > 0$) was required in the first patient study for accurately modeling FDG TACs in the liver. Neglecting $k_4$ in the model reduced TAC fit quality with higher AIC values (results not shown). Compared with the image-derived SBIF, the optimization-derived DBIF significantly increased the mean values of $K_1$ (0.5112 vs 0.9829), $k_2$ (0.4983 vs 1.1053), $k_3$ (0.0008 vs 0.0141) and $K_i$ (0.0008 vs 0.0119), all with p<0.0001. The difference in $K_1$ in individual patient was 101% on average and up to 150%, as shown in FIG. 9. Compared with the population-based DBIF, the optimization-derived DBIF significantly increased the mean values of $k_3$ (0.0011 vs 0.0141, p<0.0001), $k_4$ (0.0196 vs 0.0534, p=0.0034) and $K_i$ (0.0010 vs 0.0119, p<0.0001). Although the mean values of $K_1$ by the optimization-derived and population-based DBIF models are similar to each other (0.9787 vs. 0.9829), $K_1$ values by the two models were very different in each individual patient (FIG. 9). The change was 27% on average and up to 44%.

Association with Histopathologic Data

Figure 10A:
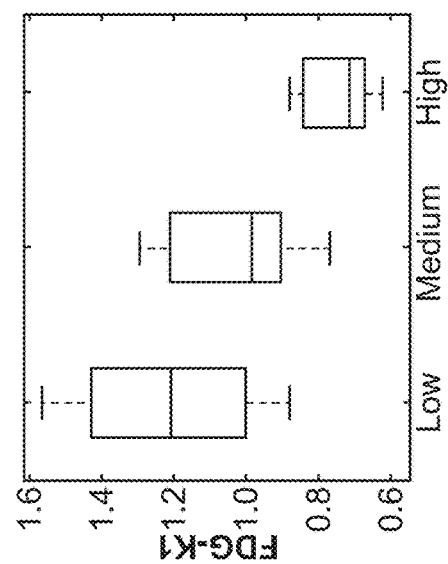
FIG. 10A shows association of histopathological inflammation score with FDG $K_1$ estimated by an image-derived single blood input function, according to various embodiments.
Figure 10B:
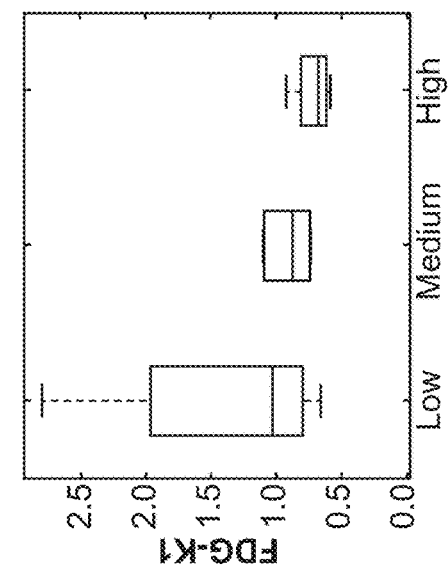
FIG. 10B shows association of histopathological inflammation score with FDG $K_1$ estimated by a population-based dual blood input function, according to various embodiments.
Figure 10C:
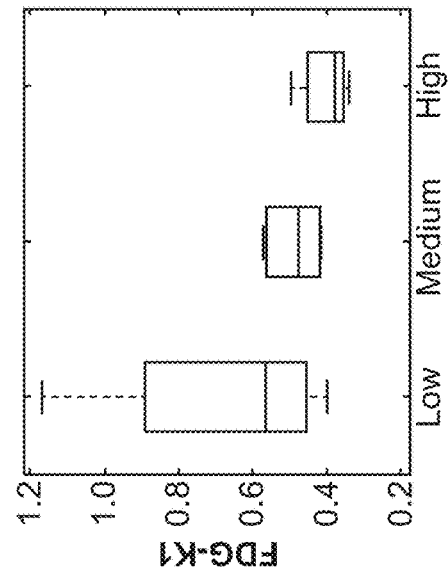
FIG. 10C shows association of histopathological inflammation score with FDG $K_1$ estimated by optimization-derived dual blood input function, according to various embodiments.

FIG. 10 shows the associations of histopathologic grades of liver inflammation with FDG $K_1$ by different input models. The standard boxplots reflect the median, 25% percentile and 75% percentile of $K_1$ in each of low, medium and high inflammation groups. Overall, FDG $K_1$ value decreased as inflammation grade increased. The results of statistical t test for comparing group means and U test for comparing group medians are summarized in Table 3. Neither the SBIF model nor the population-based DBIF model could differentiate low, medium and high inflammation groups (p>0.05). In comparison, $K_1$ by the optimization-derived DBIF model was better associated with the inflammation grades and differentiated low versus high inflammation groups and medium versus high inflammation groups (p<0.05).

Determination of liver inflammation in NAFLD/fatty liver disease patients is crucial in differentiating NASH from simple hepatic steatosis. Dynamic FDG-PET with kinetic modeling has the potential to provide a noninvasive imaging biomarker for characterizing hepatic inflammation. Accurate kinetic modeling of dynamic liver FDG-PET data requires consideration of the effect of dual-blood supplies in the liver. Although the input function from the hepatic artery can be derived from the aorta in the dynamic images, it is difficult to derive the portal vein input function from dynamic PET because the size of portal vein (10-15 mm) is small compared to the spatial resolution of clinical PET scanner (4-8 mm). Partial volume effects, noise and respiratory motion all can contaminate the accuracy of the portal vein input function.

The standard SBIF model simply neglects the portal vein input and therefore provides inaccurate estimation of FDG kinetic parameters. The $K_1$ parameter, which is the major parameter of interest for liver inflammation, is generally underestimated by SBIF, as demonstrated in this study. To account for the dual-blood effect, the population-based DBIF model was applied in the first patient study.

The optimization-derived DBIF model provided the best performance according to TAC fitting quality and association with histopathological inflammation grades. Because the parameters of the input model were jointly estimated with liver tissue kinetic parameters, the estimation was more adaptive to individual patients and achieved lower AIC and higher F values. In the first patient study, the two DBIF model parameters $k_a$ and $f_A$ were 1.627±1.427 and 0.044±0.054. The $f_A$ estimates were far smaller than the population mean 0.25 that was reported based on arterial sampling. This may be explained by the difference between image-derived input function and arterial blood input. The resulting $K_1$ parameter estimates were significantly different from those by SBIF and optimization-based DBIF. Although there was no ground truth of $K_1$ values for validating the estimates, evaluation of statistical information criteria and analysis of association of $K_1$ with liver inflammation grades provided a feasible way to prove the superior performance of the modified DBIF model.

TABLE 3

P values of t test and U test for comparing in different liver inflammation groups using FDG $K_1$ estimated by SBIF, population-based (PB) DBIF, and optimization-derived (OD) DBIF.

| | T test | | | U test | | |
|---|---|---|---|---|---|---|
| Group Comparison | SBIF | DBIF-PB | DBIF-OD | SBIF | DBIF-PB | DBIF-OD |
| Low vs. medium inflammation | 0.2733 | 0.3158 | 0.3121 | 0.5556 | 0.5556 | 0.5556 |
| Medium vs. high inflammation | 0.0826 | 0.0941 | 0.0242 | 0.1508 | 0.1508 | 0.0317 |
| Low vs. high inflammation | 0.1206 | 0.1707 | 0.0116 | 0.0635 | 0.1905 | 0.0317 |

Embodiments provide validation of kinetic modeling using histopathological reference. No studies had demonstrated an impact on physiological measurements using a histopathological ground truth. Embodiments provided the first direct evidence on the impact of DBIF on improving association of the FDG-PET biomarker with histopathological inflammation in human patients.

In the first patient study, three different kinetic models for analyzing dynamic FDG-PET data for characterizing liver inflammation are examined. Statistical fit quality metrics and analysis of association with histopathology indicated modeling of dual-blood input function is crucial for accurate kinetic modeling of liver time activity curves. The optimization-derived DBIF model improved the association of FDG $K_1$ with liver inflammation grades and was more appropriate than traditional single-blood input function and population-based DBIF for dynamic FDG-PET kinetic analysis in human NASH studies.

EXAMPLE 2

Study Design and Population:

The second patient study is designed as a cross-sectional study in patients with fatty liver disease who have or will undergo a liver biopsy as a part of routine clinical care or for enrollment in clinical trials. All patients underwent the imaging study (PET scan) within 6 months of the liver biopsy. The preferable time for the imaging was at least 2 weeks after the liver biopsy and within 3 months. The 2-week delay from the biopsy was to allow time for any local post-biopsy inflammation to subside. Baseline clinical and laboratory values, of the patients who are enrolled, are recorded. All patients also underwent magnetic resonance-proton density fat fraction (MR-PDFF) on the same day as the PET scan to quantitate hepatic fat by MRI. MR elastography (MRE) was performed to determine fibrosis.

Inclusion and Exclusion Criteria:

Patients with a diagnosis of fatty liver disease, undergoing a liver biopsy, >18 years age and able to provide informed consent were eligible to enroll in the study. Pregnant patients and prisoners were excluded from the study. Other exclusions were history of alcohol abuse, chronic hepatitis B or C, or other chronic liver disease other than non-alcoholic fatty liver disease. Although $^{18}$F-FDG is safe and widely used with excellent safety profile, history of any allergy to $^{18}$F-FDG or inability to lie in the PET scanner for approximately one hour were exclusionary.

Objectives of the Study:

This is a proof-of-concept study with the primary objective to identify an FDG-PET biomarker of hepatic inflammation. This is achieved by comparing the FDG kinetic parameters in patients with biopsy-determined hepatic inflammation score (sum of lobular inflammation and ballooning degeneration) and combined NAFLD activity score (NAS). The distribution of the inflammation may be analyzed by visualizing and quantitating kinetic parameters in the liver lobes and segments. The secondary objective is to identify an FDG-PET biomarker of hepatic steatosis by comparing FDG-PET parameters with steatosis score determined by biopsy and by MR-PDFF.

Liver Histology:

Liver biopsies were deemed adequate according to National guidelines and scored according to the nonalcoholic steatohepatitis clinical research network (NASH-CRN) by single expert pathologist. All biopsies were acquired under ultrasound guidance and the segment biopsied was noted. Biopsies will be stained as per current standards. Steatosis location (0-zone 3, 1-zone 1, 2-azonal, 3-panacinar) will be recorded. Steatohepatitis and steatosis combined scores termed the NAFLD activity score (NAS) developed by the NASH-CRN cohort. NAS is comprised of severity of steatosis (0-3), inflammation (0-3), and hepatocellular ballooning (0-2). Although combined NAS≥4 has been reported to correlate with the presence of NASH, the scores of lobular inflammation and ballooning degeneration are noted to represent hepatic inflammation. Lobular inflammation score and ballooning degeneration scores were combined to give the overall 'hepatic inflammation' score. A sum of score of ≥3 was deemed as high inflammation. Liver fibrosis was assessed using Kleiner fibrosis scales, as has been described previously.

PET Scan and Tracer Kinetic Modeling:

Dynamic $^{18}$F-FDG PET Modeling: Dynamic $^{18}$F-FDG PET studies were performed with the GE Discovery 690 PET/CT scanner. Diabetic patients were instructed to hold their long-acting insulin dose after midnight and morning dose of short acting insulin. Pre-PET blood glucose was measured for all patients. Each patient was injected with 10 mCi FDG. List-mode data acquisition started right after the intravenous bolus administration and lasted for one hour. At the end of PET scan, a low-dose CT scan is performed for attenuation correction for PET. The total effective radiation dose from the PET/CT scan was approximately 7.5 mSv. The dynamic PET data were binned into 49 time frames using the sampling schedule: 30×10 s, 10×60 s, and 9×300 s. Dynamic PET images are reconstructed using a software with the ordered subsets expectation maximization (OSEM) algorithm.

Tracer Kinetic Modeling: Eight spherical regions of interest (ROI), each with 25 mm in diameter, were placed on the eight segments of the liver excluding the caudate lobe. These ROI placements were tuned and confirmed by an experienced MRI radiologist. The averaged FDG activity in the combined liver ROI was extracted from the dynamic sequence to form a time activity curve of the liver. An additional ROI is placed in the descending aorta region to extract image-derived blood input function. A kinetic modeling package is used to estimate the kinetic parameters based on the predetermined 3-compartment model (FIG. 5). The modeling algorithm has also employed an additional compartment to correct the dispersion effect caused by the dual blood supply system in the liver. Four different micro kinetic parameters, $K_1$, $k_2$, $k_3$, $k_4$, which represent the FDG transport rate constant between compartments (indicated in FIG. 5), and a macro parameter, $K_i=K_1*k_3/(k_2+k_3)$, which indicates the overall FDG net influx rate, were included in statistical correlation analysis with histologic scores. Standardized uptake value (SUV) at one-hour post FDG injection was also calculated using the standard formula. SUV ratio (SUVR) was calculated as the ratio of liver SUV over blood SUV to adjust for body factors.

Statistical Analysis

Pearson correlation coefficients for the association between kinetic parameters and both hepatic inflammation score and NAS score, along with their 95% confidence intervals were calculated. To compare the kinetic parameters in patients with low (<3) and high inflammation (≥3) or low (≤4) or high (>4) NAS score, a 2-sample t-test at the 0.05 level (2-sided) was used. Clinical characteristics of patients were shown using frequencies and percentages as appropriate.

Results:

Patient Characteristics

Figure 11:
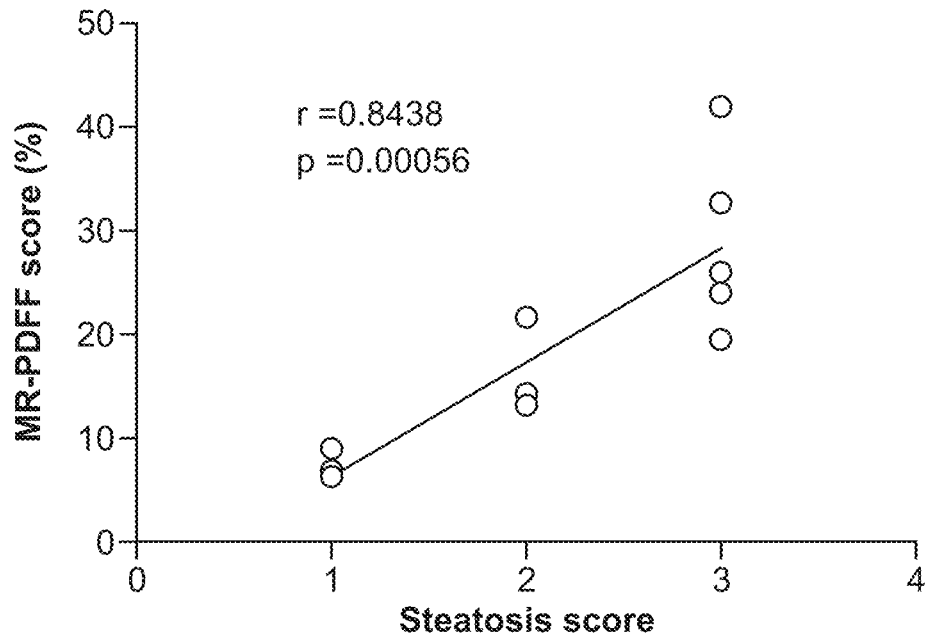
FIG. 11 shows a correlation between magnetic resonance-proton density fat fraction (MR-PDFF) and steatosis score, according to various embodiments.
Figure 12:
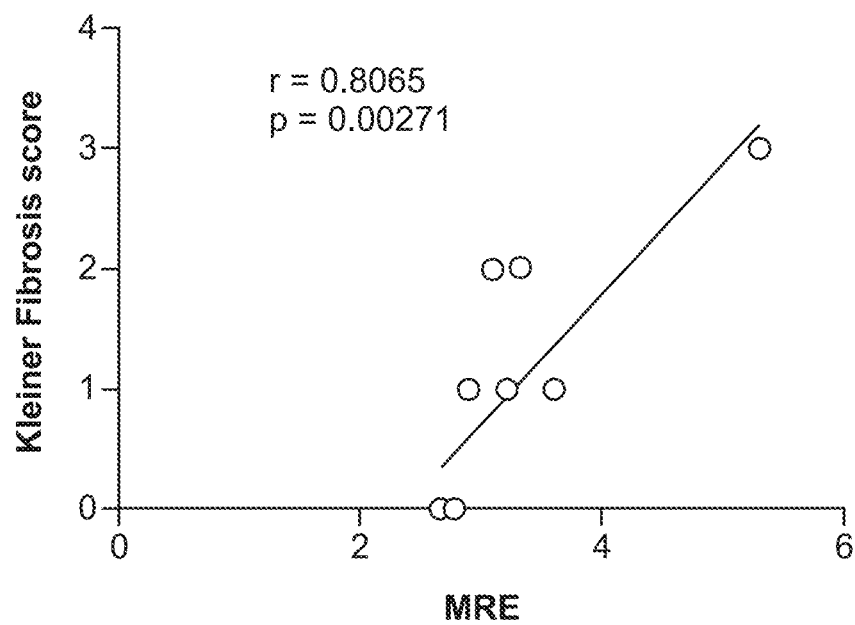
FIG. 12 shows a correlation between magnetic resonance elastography (MRE) and histological fibrosis score, according to various embodiments.

Twelve patients undergoing liver biopsy were enrolled and underwent dynamic $^{18}$F-FDG PET imaging and MRI for fat quantification by MR-PDFF and for fibrosis quantification by MRE An expert pathologist read the liver biopsies according to NASH-CRN criteria and was blinded to the PET scan and MRI findings. The mean time of PET scan from liver biopsy was 9.4 weeks (range: 3.9-17.9 weeks). Table 4a shows the baseline demographics and biochemical characteristics of the patients. Majority of the patients were white (75%) while 25% were Hispanics. Female patients formed 67% of the cohort with 75% of the patients between the ages 40-70 years and 25% between 18-39 years. The mean BMI was 33.7±6.0 kg/m$^2$ (range: 25.3-43.1 kg/m$^2$) and mean waist circumference was 110.1±11.8 cm (range: 94-127 cm). Three of the patients had diabetes mellitus, 8 had hypertension and six patients had hyperlipidemia; with two patients having all three. Four patients were on metformin (one for presumed hyperinsulinemia but was non-diabetic). The mean fasting glucose prior to PET scan ranged 115±33 mg/dL (range: 92-202 mg/dL). Table 4b shows the histologic characteristics of the patients. Grade 2-3 steatosis was noted in 83% of the patients. Most patients had stage 0 or 1 (1a/1b/1c) fibrosis (75%) with stage 2 fibrosis in 2 patients and stage 3 fibrosis in 1 patient. The patient population had an equitable spread across NAS score (≥5 of 58%). 67% of patients had hepatic inflammation sore of ≥3. Internal validity of the biopsy readings was tested by correlation with MR-PDFF and MRE scores. As shown in FIG. 11 and FIG. 12, there was significant correlation between histologic scores for steatosis (r=0.8438; p=0.0006) and fibrosis (r=0.8065; p=0.00271) compared with MR-PDFF (% fat fraction) and MRE (kPa), respectively.

TABLE 4a

Baseline Demographics and Biochemical Characteristics of Patients

| Characteristics | n | % of total |
|---|---|---|
| Overall: | 12 | 100% |
| Age: | | |
| 18-40 | 3 | 25% |
| >40-70 | 9 | 75% |
| >70 | 0 | 0% |
| Gender: | | |
| Male | 4 | 33% |
| Female | 8 | 67% |
| Race/Ethnicity: | | |
| White | 9 | 75% |
| Hispanics | 3 | 25% |
| Others | 0 | 0% |
| BMI: | | |
| ≤24.9 | 1 | 8% |
| 25-29.9 | 2 | 17% |
| 30-39.9 | 7 | 58% |
| ≥40 | 2 | 17% |
| Waist circumference: | | |
| <102 cm | 4 | 33% |
| ≥102 cm | 8 | 67% |
| ALT | | |
| <40 | 3 | 25% |
| 40-120 | 6 | 50% |
| >120 | 3 | 25% |
| Diabetes Mellitus presence: | | |
| Yes | 3 | 25% |
| No | 9 | 75% |
| Pre-PET scan fasting blood glucose (mg/dL) | | |
| <100 | 2 | 17% |
| 100-125 | 8 | 66% |
| >125 | 2 | 17% |
| NAFLD Fibrosis Score: | | |
| <-1.455 | 0 | 0% |
| -1.455-0.675 | 4 | 33% |
| >0.675 | 8 | 67% |

TABLE 4b

Histologic Characteristics of Patients

| Characteristics | n = 12 | % of total |
|---|---|---|
| Steatosis (0-3): | | |
| Grade 0, 1 | 2 | 17% |
| Grade 2, 3 | 10 | 83% |
| Inflammation (Lobular inflammation + ballooning degeneration) (0-5): | | |
| <3 | 4 | 33% |
| ≥3 | 8 | 67% |
| Fibrosis (Kleiner score): | | |
| 0, 1a, 1b | 9 | 75% |
| 2, 3, 4 | 3 | 25% |
| NAFLD activity score (NAS) (0-8): | | |
| 0-4 | 5 | 42% |
| 5-8 | 7 | 58% |

Figure 13:
FIG. 13 shows a representative dynamic FDG PET $K_1$ image with three exemplary ROIs, according to various embodiments.
Figure 15:
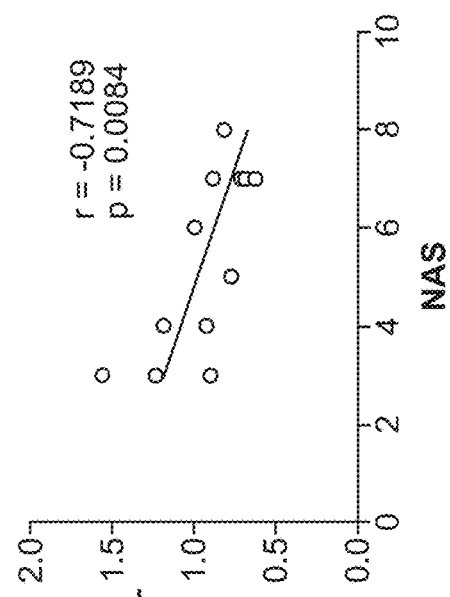
FIG. 15 shows a correlation between FDG $K_1$ and an NAFLD activity score, according to various embodiments.
Figure 14:
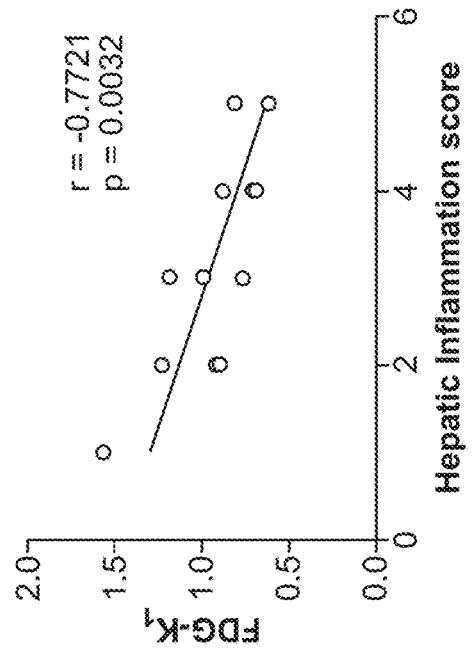
FIG. 14 shows a correlation between FDG $K_1$ and a hepatic inflammation score, according to various embodiments.

FDG Micro-kinetics and Liver Inflammation:

Utilizing tracer kinetic modeling noted above, the transport kinetics of $^{18}$F-FDG was measured (FIG. 5). $K_1$ measures the transport of FDG from blood to hepatic tissue, reflecting both blood flow and the expression of glucose transporters. As noted above, $K_1$ is calculated from an aggregate of the values from each of the eight liver segments where a spherical ROI of 25 mm was placed as shown in a representative image (FIG. 13). Hepatic inflammation was measured as sum of the histologic scores for lobular inflammation and ballooning degeneration determined according to NASH-CRN criteria. NAFLD activity score (or NAS) was the sum of steatosis and hepatic inflammation. As shown in FIG. 14, FDG $K_1$ significantly correlated with the hepatic inflammation score (r=-0.7721, p=0.0032). $K_1$ was also noted to correlate significantly with the overall NAS score (r=-0.7189, p=0.0084; FIG. 15). $K_1$ values from the liver segment with the highest value correlated equally with the histologic hepatic inflammation score (r=-0.7611, p=0.0032). $K_1$ values decreased as the hepatic inflammation and NAS scores increases.

Other micro kinetic parameters, $k_2$ (release), $k_3$ (phosphorylation), $k_4$ (dephosphorylation), which represent the FDG transport rate constant between compartments (indicated in FIG. 5), and a macro parameter, $K_i=K_1*k_3/(k_2+k_3)$, which indicates the overall FDG influx rate, were calculated. SUV at one-hour post FDG injection was also calculated. SUV and $K_i$ are the most widely used parameters for characterizing the overall glucose utilization. As shown in Table 5 and FIGS. 16A-E, the kinetic parameters $k_2$ (r=−0.4857; p=0.1094), $k_3$ (r=0.3436; p=0.2742), $k_4$ (r=−0.09191; p=0.7763) did not correlate with hepatic inflammation. Neither was there correlation of $K_i$ (r=0.1872; p=0.5603) or SUV (r=0.288; p=0.364) with histologic hepatic inflammation.

TABLE 5

Summary of FDG kinetic parameters and correlation with Hepatic inflammation and NAS

| FDG Kinetic Parameters | Hepatic Inflammation | | NAS | |
|---|---|---|---|---|
| | r | p-value | r | p-value |
| $K_1$ | −0.7721 | 0.0032* | 0.7189 | 0.0084* |
| $k_2$ | −0.4857 | 0.1094 | −0.3973 | 0.2009 |
| $k_3$ | 0.3436 | 0.2742 | 0.47 | 0.1231 |
| $k_4$ | −0.0919 | 0.7763 | 0.0192 | 0.9526 |
| $K_i$ | 0.1872 | 0.5603 | 0.3149 | 0.3188 |
| SUV | 0.288 | 0.364 | 0.1881 | 0.5582 |

*p < 0.05

Distribution of $K_1$ in the Liver

Figures 17A, 17B, 17C:
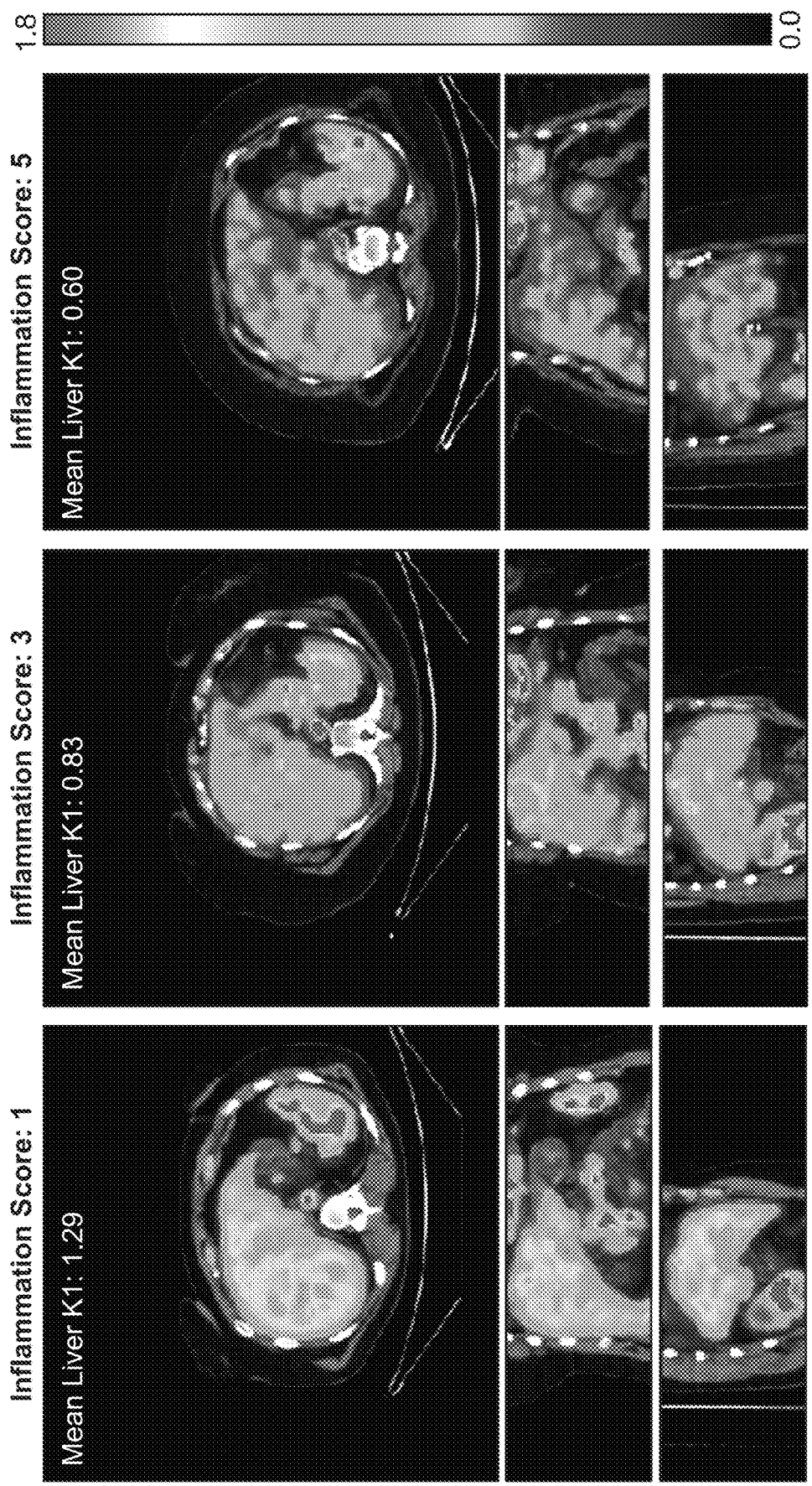
FIG. 17 shows three illustrations of $K_1$ distribution by histological inflammation, according to various embodiments.
Figure 19A:
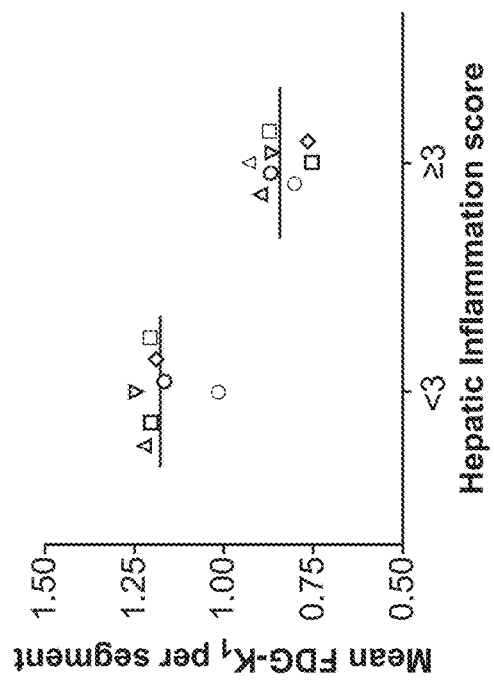
FIG. 19A shows segmental $K_1$ values in patients with low and high inflammation scores, according to various embodiments.
Figure 19B:
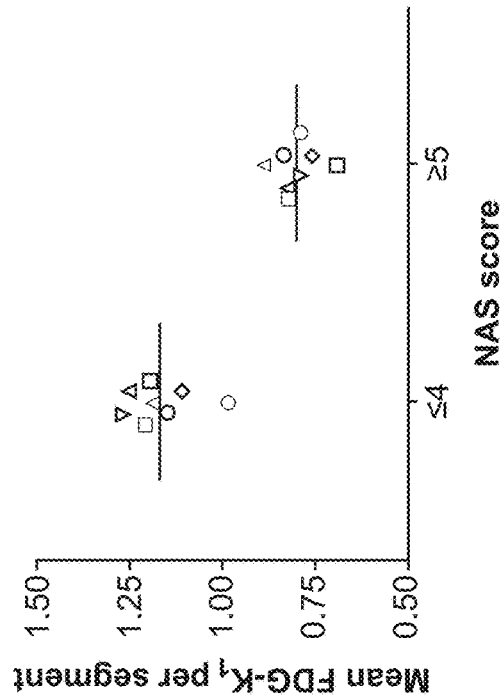
FIG. 19B shows segmental $K_1$ values in patients with low and high NAS scores, according to various embodiments.
Figure 18:
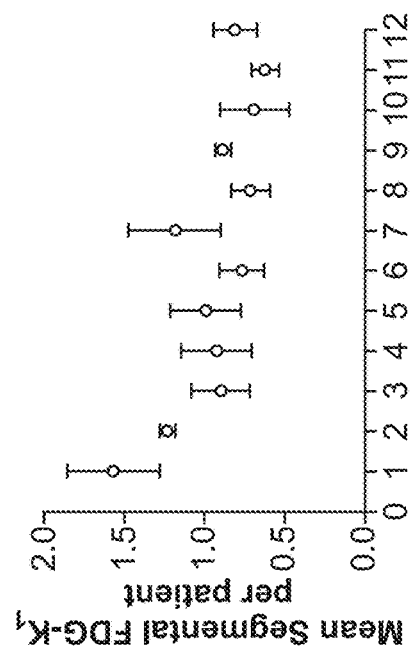
FIG. 18 shows variability in $K_1$ values between segments in each patient, according to various embodiments.

Distribution of disease in patients with NASH is believed to be heterogeneous in distribution. The heterogeneity of $K_1$ values is evaluated across the eight liver segments measured. The $K_1$ values were noted to be heterogeneous between segments amongst individual patients. A representative image is shown in FIG. 17 depicting images of three patients with increasing histologic inflammation scores where heterogeneity in FDG uptake is visualized between the segments. The mean $K_1$ value with standard deviation of $K_1$ values between segments is shown in FIG. 18. The median standard deviation of $K_1$ values between segments of the 12 patients was 0.16 (range: 0.05-0.29). The mean $K_1$ from each segment of all patients showed a distinct segregation amongst those with low (<3) or high (≥3) inflammation (FIG. 19A) or low (≤4)/high (>4) NAS (FIG. 19B) scores.

FDG-PET Correlations with Steatosis Measurements by Histology and MRI

Exploratory analysis was done of FDG-PET measures of glucose uptake. Table 6 lists the FDG kinetic parameters and its correlation with hepatic steatosis and MR-PDFF scores. SUV did not correlate with either histologic steatosis (r=−0.0148, p=0.9636) or MR-PDFF (r=−0.0337, p=0.9173). Instead, SUV ratio (SUVR), which was calculated by as the ratio of liver SUV over blood SUV to adjust for body factors, was significantly correlated with hepatic steatosis by biopsy scoring (r=−6016; p=0.0385) and MR-PDFF (r=−0.6916; p=0.0127). Among different FDG kinetic parameters, $K_1$ and $k_3$ tended to correlate with the histologic steatosis and with MR-PDFF but did not achieve significance. Other parameters $k_2$, $k_4$ and $K_i$ did not correlate with steatosis by histology or by MR-PDFF.

TABLE 6

Summary of FDG kinetic parameters and correlation with hepatic steatosis by biopsy and by MR-PDFF

| FDG Kinetic Parameters | Hepatic Steatosis | | MR-PDFF | |
|---|---|---|---|---|
| | r | p-value | r | p-value |
| $K_1$ | −0.4686 | 0.1244 | −0.5219 | 0.0817 |
| $k_2$ | −0.1813 | 0.5729 | −0.2681 | 0.3995 |
| $k_3$ | 0.5307 | 0.0759 | 0.4578 | 0.1346 |
| $k_4$ | 0.1819 | 0.5716 | 0.2925 | 0.3561 |
| $K_i$ | 0.4211 | 0.1728 | 0.3621 | 0.2475 |
| SUV | −0.0148 | 0.9636 | 0.0337 | 0.9173 |
| SUVR | −0.6016 | 0.0385* | −0.6916 | 0.0127* |

*p < 0.05

EXAMPLE 3

Study Design and Population:

The third patient study is designed as a cross-sectional study of patients with fatty liver disease who have undergone or will undergo a liver biopsy. The time window for the imaging studies ranged from 2 weeks (to allow time for any local post biopsy inflammation to subside) to 6 months after liver biopsy was performed. The baseline clinical and laboratory values of the patients enrolled in the study were recorded. All patients also underwent MRI proton-density fat fraction (PDFF) to quantitate hepatic fat using MRI in accordance with predetermined criteria. MR elastography (MRE) was performed to evaluate liver stiffness.

Inclusion and Exclusion Criteria

Patients older than 18 years who had a diagnosis of fatty liver disease, were undergoing liver biopsy, and were able to provide informed consent were eligible to enroll in the third patient study. Pregnant patients, prisoners, and individuals with a history of alcohol abuse, chronic hepatitis B or C, or other chronic liver disease were excluded from the third patient study. A history of any allergy to FDG or an inability to lie in the bed of the PET scanner for approximately 1 hour was considered a reason for exclusion from the study.

Study Objectives

The primary objective was to determine FDG PET kinetic parameters that correlate with histologic findings of hepatic inflammation. The secondary objective was to determine the distribution of hepatic inflammation.

Waist Circumference and Body Mass Index

A tape measure was used to determine the waist circumference using standard methods, and body mass index (BMI) was measured as weight in kilograms divided by the square of height in meters at the time that consent was given.

Liver Histologic Findings

A single expert pathologist scored the liver biopsy specimens in accordance with the histologic scoring system of the Nonalcoholic Steatohepatitis Clinical Research Network (NASH CRN). The NAFLD activity score (NAS) (combined scores for steatosis [grades 0-3], lobular inflammation [grades 0-3], and ballooning degeneration [grades 0-2]), as developed by the NASH CRN, was determined for the patients. A combined NAS of 4 or greater has been reported to correlate with the presence of NASH, whereas scores for lobular inflammation and ballooning degeneration are noted to represent hepatic inflammation. The sum of the lobular inflammation score and the ballooning degeneration score was deemed the hepatic inflammation score. A score of 3 or less was considered to denote low inflammation, whereas a score greater than 3 denoted high inflammation. Liver fibrosis was assessed using the Kleiner fibrosis stages.

MR Elastography and MR Proton-Density Fat Fraction

MRI—MRI studies were performed using a 1.5-T scanner (Optima MR450w, GE Healthcare). All patients were instructed to avoid food and water for at least 4 hours before the examination. MR images were interpreted by one radiologist trained in abdominal fellowship who had 8 years of experience.

MR elastography: An acoustic passive driver was placed over the patients' right upper quadrant and was vibrated at 60 Hz. A 2D gradient-echo pulse sequence was used with the following parameters: an axial imaging plane; number of slices, 4; slice thickness, 8 mm; spacing, 5 mm; FOV, 42 cm2; matrix, 256×64; number of excitations, 1; bandwidth, 31.25; TR/TE, 50/21.8; and flip angle, 30°. In addition, the shear-wave images were processed with an inversion algorithm to produce elastograms. ROIs were drawn over the slices, and the mean was calculated. Care was taken to exclude large hepatic vessels, the edge of the liver (which was considered one-half the width of a wave from the liver edge), and any areas of poor signal-to-noise ratio indicated on the elastogram and mask images when a phase and magnitude threshold of 5 was used.

MRI proton-density fat fraction: The MRI PDFF was determined using six gradient-echo breathhold pulse sequences (IDEAL IQ, GE Healthcare) acquired using the following parameters: an axial imaging plane; slice thickness, 12 mm; spacing, 6 mm; FOV, 50 cm2; matrix, 192×192; number of excitations, 0.68; TR/TE, 12.4/5.9; and flip angle, 7°. The PDFF was calculated by placing nine ROIs throughout the liver, with one ROI placed in each hepatic segment, and the mean was determined.

PET and Tracer Kinetic Modeling

Dynamic FDG PET: Dynamic FDG PET studies were performed using a PET/CT scanner (Discovery 690, GE Healthcare). Patients with diabetes were instructed to abstain from taking their morning dose of short-acting insulin, long-acting overnight dose of insulin, or both doses. The blood glucose level before PET was measured for all patients. Patients were positioned to allow the liver to be covered in the axial FOV ($\approx$16 cm2) of the PET/CT scanner. Each patient was injected with 370 MBq of FDG, in accordance with a routine clinical protocol. List-mode data acquisition was started right after the administration of the IV bolus and lasted for 1 hour. After PET was completed, a low-dose CT scan was obtained for attenuation correction for PET. The total effective radiation dose from the PET/CT scan was $\approx$7.5 mSv. The dynamic PET data were binned into 49 time frames by use of the following sampling schedule: 30×10 s, 10×60 s, and 9×300 s. Dynamic PET images were reconstructed using a software with use of the ordered-subsets expectation maximization algorithm.

Tracer kinetic modeling: Eight spherical ROIs, each 25 mm in diameter, were placed on the eight segments of the liver, with the caudate lobe excluded. These ROI placements were tuned and confirmed by an experienced abdominal radiologist. The time-activity curves of the eight ROIs were averaged to form a time-activity curve of the liver. An additional ROI was placed in the descending aorta region to extract the image-derived blood input function. A kinetic modeling package is used to estimate the kinetic parameters on the basis of a three-compartment model. The modeling algorithm also used an additional compartment to correct for the dispersion effect caused by the dual blood supply system in the liver. Four different microkinetic parameters that represent the FDG transport rate constant between compartments are measured: FDG transport from blood to hepatic tissue [K1], FDG transport from hepatic tissue to plasma [k2], FDG phosphorylation into FDG 6-phosphate by hexokinase in cells [k3], and FDG dephosphorylation [k4] and a macrokinetic parameter that indicates the overall FDG net influx rate (Ki), where Ki=K1×[k3/(k2+k3)]. The SUV at 1 hour after FDG injection was also calculated using the standard formula. The SUV ratio was calculated as the ratio of the liver SUV to the blood SUV, to adjust for body factors.

Statistical Analysis

Sample size—A sample size of 22 patients provides 85% power to detect a correlation of 0.6 as well as 80% power to detect an effect size of 1.5–SD difference between group mean values, at the 0.05 level (two-sided). Pearson correlation coefficients for the association between kinetic parameters and both the hepatic inflammation score and the NAS score, in addition to their 95% CIs, were calculated. To compare the kinetic parameters in patients with low (grade, $\leq$3) and high (grade, >3) inflammation or a low (grade, $\leq$4) or high (grade, >4) NAS score, mixed-effects models with a random intercept for the patient were used. To assess the association between K1 and high inflammation versus low inflammation and a high NAS score versus a low NAS score, the ROC AUC curve is estimated using logistic regression, as well as the sensitivity and specificity of an approximately optimal K1 cutpoint. The clinical characteristics of the patients were expressed as frequencies and percentages or means and SDs, as appropriate. Statistical significance was assessed at the 0.05 level (two-sided).

Results

Patient Characteristics

Figure 20A:
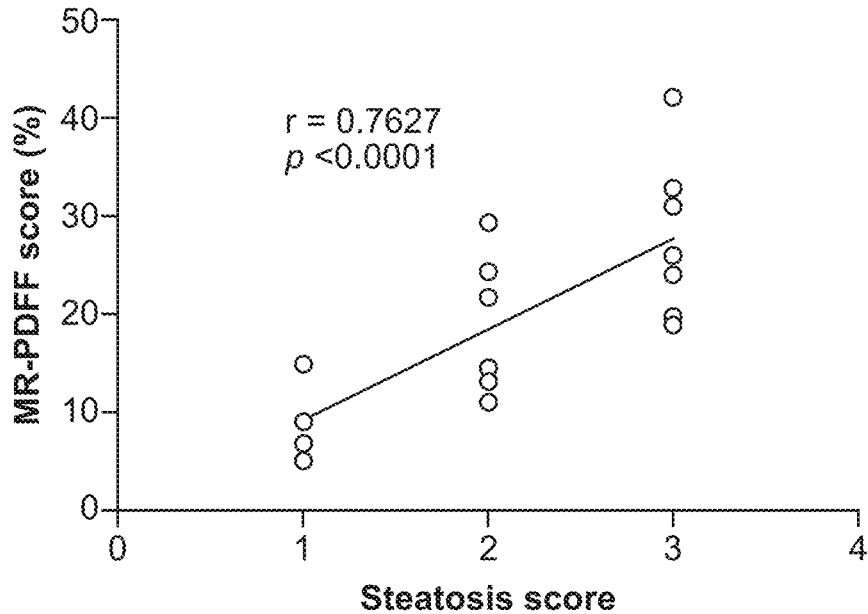
FIG. 20A illustrates a graph of correlation of MRI PDFF score with histologic steatosis score, according to various embodiments.
Figure 20B:
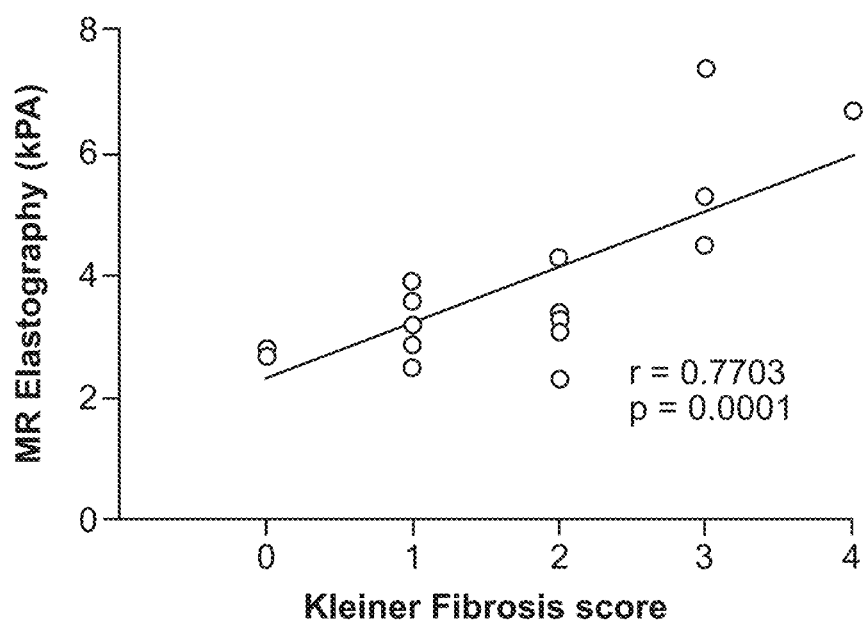
FIG. 20B illustrates a graph of correlation of MRE value with Kleiner histologic fibrosis score, according to various embodiments.

Twenty-two patients who were undergoing liver biopsy were enrolled, and all underwent dynamic FDG PET and MRI (MRI PDFF and MRE). The mean interval from liver biopsy to PET and MRI was 8.1±4.1 weeks. Table 7 shows the demographic and biochemical characteristics of the patients at baseline. In brief, most patients were white or Hispanic (90%), 64% were women, and more than three-quarters of the patients were 40-70 years of age, with age ranging from 18 to 70 years among the cohort. The mean BMI was 33.2±5.2 (range, 24-43.1), and the mean waist circumference was 108.9±11.3 cm (range, 88-127 cm). Seven of the patients had diabetes mellitus, 10 had hypertension, and seven had hyperlipidemia, with two patients having all three conditions. Eight patients were taking metformin (one patient who did not have diabetes but was taking metformin for presumed hyperinsulinemia), and none were taking insulin. The mean fasting glucose level before PET was performed was 116±33 mg/dL (range, 83-202 mg/dL). Table 7 shows the histopathologic characteristics of the patients. Although most patients had steatosis of grade 2 or 3, distribution of hepatic inflammation scores (grade, $\leq$3 or >3) and fibrosis scores was equitable. The internal validity of the biopsy readings was tested by correlation with MRI PDFF and MRE scores because these values were well established. FIGS. 20A-20B illustrate the correlation of MRI proton-density fat fraction (PDFF) and MR elastography (MRE) with histologic steatosis and fibrosis scores. Circles denote individual patient's PDFF scores, and solid line denotes slope. FIG. 20A illustrates a graph of correlation of MRI PDFF score with histologic steatosis score. FIG. 20B illustrates a graph of correlation of MRE value with Kleiner histologic fibrosis score. As shown in FIGS. 20A-20B, significant correlation was noted between histopathologic scores for steatosis (r=0.7627; p<0.0001) and fibrosis (r=0.7703; p=0.0001), compared with MRI PDFF (expressed as percentage fat fraction) and MRE value (expressed as kilopascals), respectively.

TABLE 7

Baseline Demographics, Biochemical and Histologic Characteristics of Patients

| Characteristics | n | % of total |
|---|---|---|
| Overall: | 22 | 100% |
| Age: | | |
| 18-39 | 4 | 18% |
| >40-69 | 16 | 73% |
| >70 | 2 | 9% |
| Gender: | | |
| Male | 8 | 36% |
| Female | 14 | 64% |
| Race/Ethnicity: | | |
| White | 14 | 64% |
| Hispanics | 6 | 27% |
| Others | 2 | 9% |
| BMI: | | |
| ≤24.9 | 2 | 9% |
| 25-29.9 | 4 | 18% |
| 30-39.9 | 14 | 64% |
| ≥40 | 2 | 9% |
| Waist circumference: | | |
| <102 cm | 7 | 32% |
| ≥102 cm | 15 | 68% |
| ALT | | |
| <40 | 7 | 32% |
| 40-120 | 11 | 50% |
| >120 | 4 | 18% |
| Diabetes Meilitus presence: | | |
| Yes | 7 | 32% |
| No | 15 | 68% |
| Pre-PET scan fasting blood glucose (mg/dL) | | |
| <100 | 8 | 36% |
| 100-125 | 10 | 46% |
| >125 | 4 | 18% |
| NAFLD Fibrosis Score: | | |
| <-1.455 | 2 | 9% |
| -1.455-0.675 | 7 | 32% |
| >0.675 | 13 | 59% |
| Steatosis (0-3): | | |
| Grade 0, 1 | 7 | 32% |
| Grade 2, 3 | 15 | 68% |
| Inflammation (Lobular inflammation + ballooning degeneration) (0-5): | | |
| <3 | 13 | 59% |
| ≥3 | 9 | 41% |
| Fibrosis (Kleiner score): | | |
| 0, 1a, 1b | 13 | 59% |
| 2, 3, 4 | 9 | 41% |
| NAFLD activity score (NAS) (0-8): | | |
| 0-4 | 8 | 36% |
| 5-8 | 14 | 64% |

FDG Microkinetics and Liver Inflammation

Figure 21A:
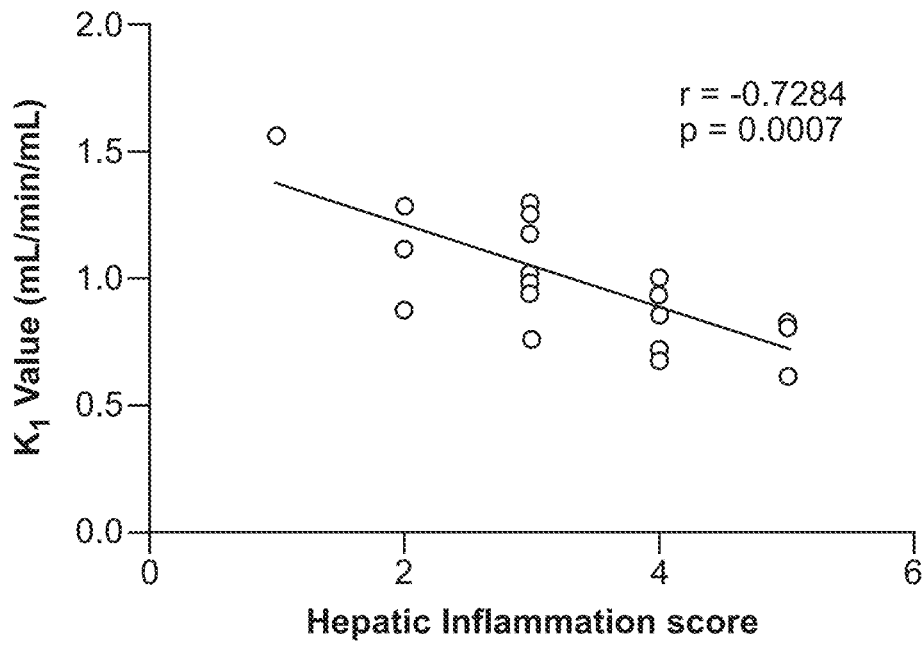
FIG. 21A illustrates correlation between FDG K1 and a hepatic inflammation score, according to various embodiments.
Figure 21B:
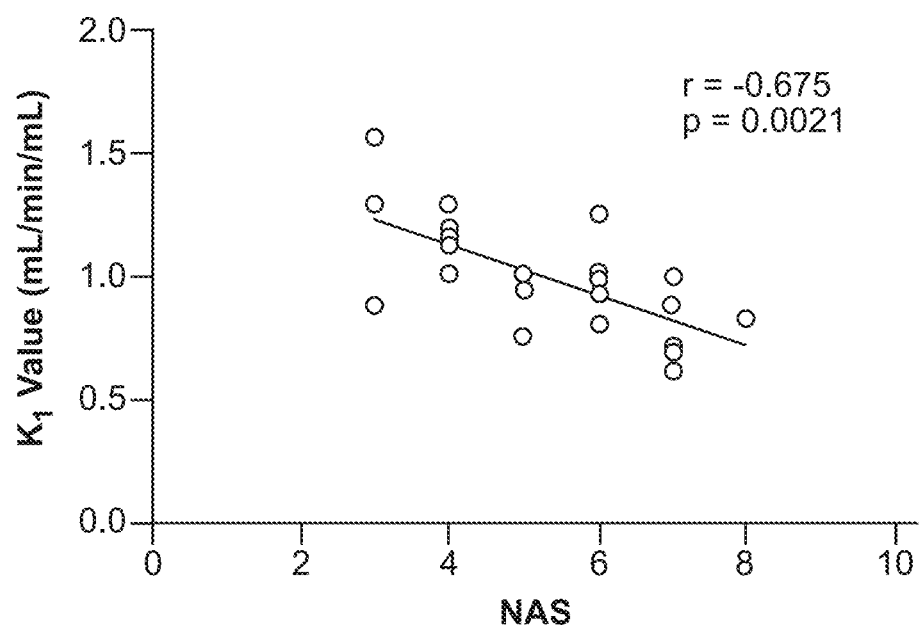
FIG. 21B shows a correlation between FDG K1 and a NAS score, according to various embodiments.
Figure 22A:
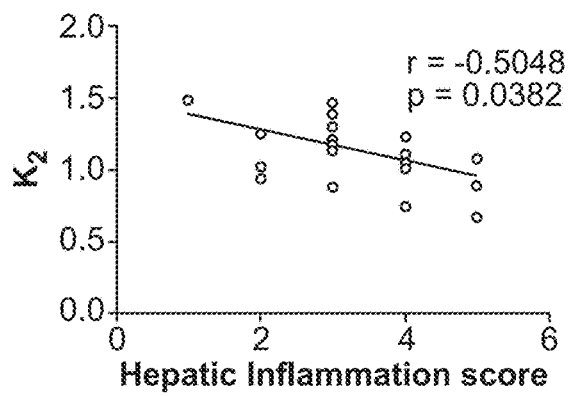
FIG. 22A illustrates a graph of correlation of histologic hepatic inflammation with rate of FDG transport from hepatic tissue to plasma (k2), according to various embodiments.
Figure 22B:
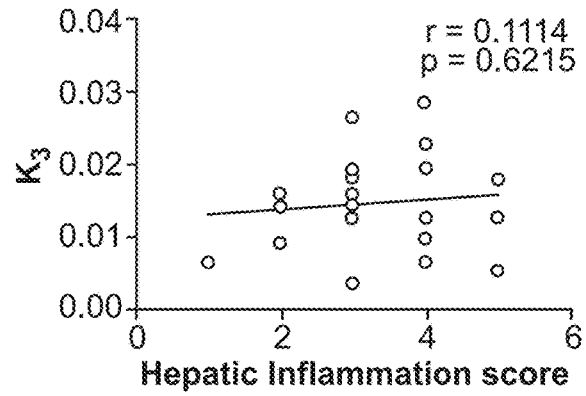
FIG. 22B illustrates a graph of correlation of histologic hepatic inflammation with rate of FDG phosphorylation into FDG 6-phosphate by hexokinase in cells (k3), according to various embodiments.
Figure 22C:
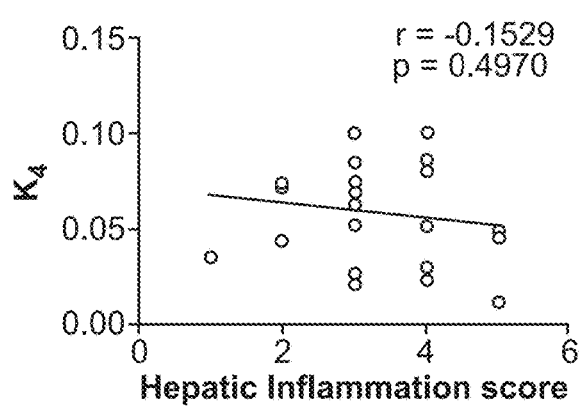
FIG. 22C illustrates a graph of correlation of histologic hepatic inflammation with rate of FDG dephosphorylation (k4), according to various embodiments.
Figure 22D:
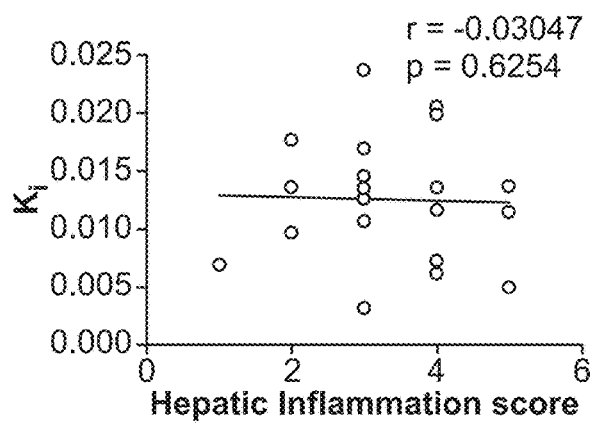
FIG. 22D illustrates a graph of correlation of histologic hepatic inflammation with FDG net influx rate (Ki), according to various embodiments.
Figure 22E:
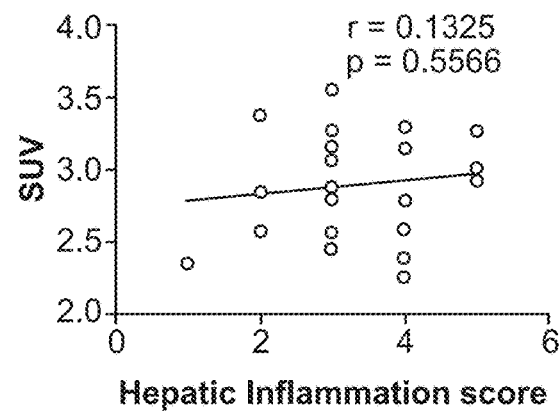
FIG. 22E illustrates a graph of correlation of histologic hepatic inflammation with SUV, according to various embodiments.

K1 significantly correlated with the hepatic inflammation score (r=−0.7284; p=0.0001) (FIG. 21A). K1 was also noted to correlate significantly with the overall NAS score (r=−0.675; p=0.0006) (FIG. 21B). K1 values were inversely related to hepatic inflammation and NAS. FIGS. 22A-22E illustrate the correlation of histologic hepatic inflammation with microkinetic parameters, macrokinetic parameters, and standardized uptake value (SUV). Circles denote individual patient's FDG kinetics, and solid line denotes score. FIG. 22A illustrates a graph of correlation of histologic hepatic inflammation with rate of FDG transport from hepatic tissue to plasma (k2). FIG. 22B illustrates a graph of correlation of histologic hepatic inflammation with rate of FDG phosphorylation into FDG 6-phosphate by hexokinase in cells (k3). FIG. 22C illustrates a graph of correlation of histologic hepatic inflammation with rate of FDG dephosphorylation (k4). FIG. 22D illustrates a graph of correlation of histologic hepatic inflammation with FDG net influx rate (Ki). FIG. 22E illustrates a graph of correlation of histologic hepatic inflammation with SUV. As shown in Table 8 and FIGS. 22A-22E, the kinetic parameters k3 (r=0.1114; p=0.6215) or k4 (r=−0.1529; p=0.4970) did not correlate with hepatic inflammation. In addition, no correlation of Ki (r=0.0305; p=0.8929) or SUV (r=0.1325; p=0.5566) with histologic hepatic inflammation was noted. Weak correlation was noted between k2 and hepatic inflammation (r=−0.5048; p=0.0382) between K2 and NAS (r=−0.4325; p=0.0444).

TABLE 8

Summary of FDG kinetic parameters and correlation with Hepatic inflammation and NAS

| FDG Kinetic Parameters | Hepatic Inflammation | | NAS | |
|---|---|---|---|---|
| | r | p-value | r | p-value |
| $K_1$ | −0.7284 | 0.0001* | −0.675 | 0.0006* |
| $k_2$ | −0.5048 | 0.0382* | −0.4325 | 0.0444* |
| $k_3$ | 0.1114 | 0.6215 | 0.148 | 0.5109 |
| $k_4$ | −0.1529 | 0.4970 | −0.0851 | 0.7066 |
| $K_i$ | −0.0305 | 0.8929 | −0.02384 | 0.9161 |
| SUV | 0.1325 | 0.5566 | 0.0663 | 0.7693 |

*p < 0.01

ROC Analysis

Figure 23B:
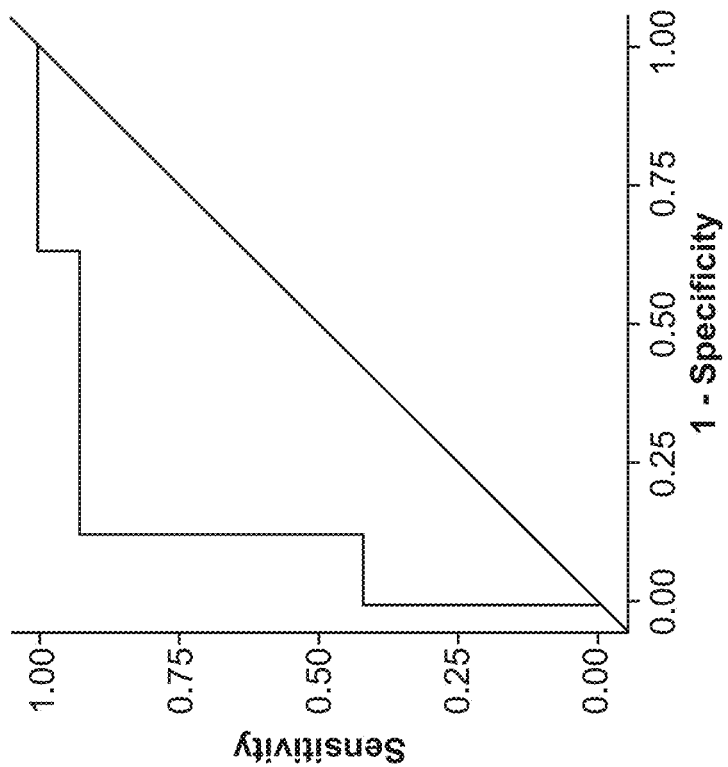
FIG. 23B illustrates ROC AUC curve of association between K1 and high versus low nonalcoholic fatty liver disease activity score, according to various embodiments.
Figure 23A:
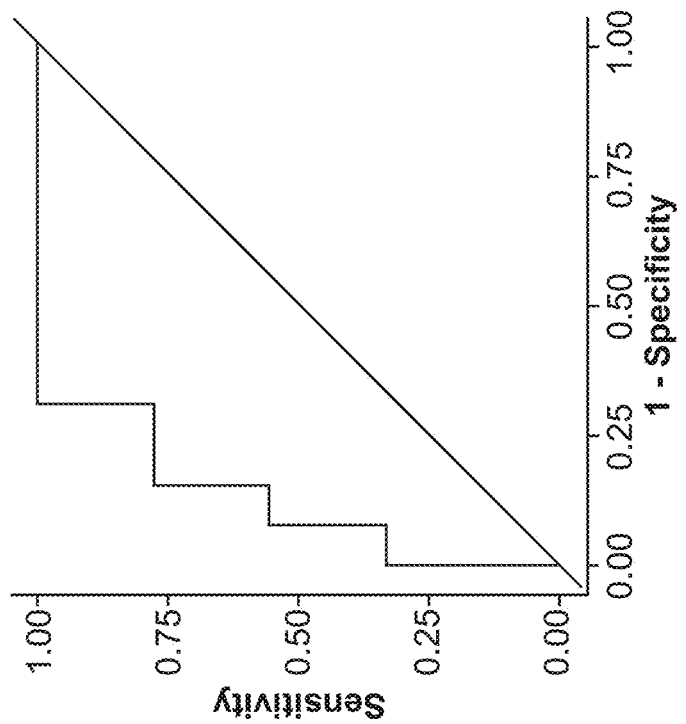
FIG. 23A illustrates ROC AUC curve of association between K1 and high versus low inflammation, according to various embodiments.

K1 had a strong association with both inflammation (ROC AUC value, 0.88) and the NAS score (ROC AUC value, 0.89), as is shown in FIGS. 23A-23B. FIGS. 23A-23B illustrate ROC AUC curve analyses of associations with rate of FDG transport from blood to hepatic tissue (K1), as performed using logistic regression. Black line denotes ROC AUC curve, and diagonal line denotes reference. FIG. 23A illustrates ROC AUC curve of association between K1 and high versus low inflammation (ROC AUC value, 0.8803). FIG. 23B illustrates ROC AUC curve of association between K1 and high versus low nonalcoholic fatty liver disease activity score (ROC AUC value, 0.8929). A cutpoint of K1=0.94 mL/min/mL corresponded to sensitivity of 78% and specificity of 85% for detection of hepatic inflammation, whereas K1=1.02 mL/min/mL corresponded to sensitivity and specificity of 93% and 88%, respectively, for the NAS score.

Segmental Heterogeneity in Glucose Transport

Distribution of disease in patients with NASH is believed to be heterogeneous. The heterogeneity of K1 values is evaluated across the eight liver segments measured. FIG. 24A shows the mean (plus or minus variation) in K1 among the eight segments in each of the 22 patients. When the patients were segregated on the basis of their histologic inflammation scores (with low inflammation denoted by a score ≤3 and high inflammation by a score >3), a distinct pattern of FDG uptake was noted. The mean and median (range) of K1 values for the low inflammation group were 1.1139±0.21 mL/min/mL and 1.1220 mL/min/mL (0.7681-1.2926 mL/min/mL), respectively, compared with those for patients with high inflammation, for whom the mean was 0.8318±0.14 mL/min/mL and the median (range) was 0.83 mL/min/mL (0.6203-1.0038 mL/min/mL). The $K_1$ scores in each of the segments are shown in Table 9 and revealed an overall decrease in $K_1$ as NASH progressed. Of note, a distinct segregation existed among those with low or high inflammation (FIG. 24B) (p=0.022), and this was also noted when patients were segregated on the basis of NAS (with a low NAS of ≤4 and a high NAS of >4) (FIG. 24C) (p=0.0091).

processes affected by obesity and NAFLD. However, this static means of using FDG PET may not exploit its full potential in evaluating patients with NAFLD. On the other hand, the dynamic FDG PET (discussed herein according to various embodiments) acquires images showing FDG activity at multiple time points to monitor both spatial and temporal distributions, enabling the ability to exploit the kinetic characteristics of FDG uptake by tracer kinetic

TABLE 9

Segmental Rates of FDG Transport From Blood to Hepatic Tissue ($K_1$ Values, Unit: mL/min/mL) Segregated by Low and High Inflammation

| Segmental $K_1$ Value | $K_1$ Value (mL/min/mL) of Patients With Low Inflammation (n = 13)[a] | | $K_1$ Value (mL/min/mL) of Patients With High Inflammation (n = 9)[b] | |
|---|---|---|---|---|
| | Mean ± SD | Median (Range) | Mean ± SD | Median (Range) |
| Overall | 1.1139 ± 0.21 | 1.122 (1.56-0.77) | 0.8318 ± 0.14 | 0.8300 (1-0.62) |
| Segment 2 | 1.1126 ± 0.26 | 1.2136 (1.45-0.66) | 0.8312 ± 0.18 | 0.8292 (1.22-0.55) |
| Segment 3 | 1.0070 ± 0.37 | 0.9365 (1.9-0.37) | 0.8955 ± 0.18 | 0.8812 (1.15-0.58) |
| Segment 4A | 1.0869 ± 0.22 | 1.0815 (1.42-0.72) | 0.8849 ± 0.19 | 0.8381 (1.27-0.63) |
| Segment 4B | 1.2358 ± 0.42 | 1.1118 (2.22-0.65) | 0.8557 ± 0.23 | 0.7979 (1.30-0.62) |
| Segment 5 | 1.0372 ± 0.33 | 1.0046 (1.87-0.56) | 0.7166 ± 0.12 | 0.7827 (0.83-0.49) |
| Segment 6 | 1.0642 ± 0.31 | 0.9992 (1.6-0.59) | 0.8530 ± 0.17 | 0.9324 (1.03-0.61) |
| Segment 7 | 1.0830 ± 0.32 | 1.1965 (1.69-0.59) | 0.9433 ± 0.15 | 0.9596 (1.17-0.73) |
| Segment 8 | 1.1552 ± 0.26 | 1.1901 (1.64-0.56) | −0.9244 ± 0.16 | 0.9130 (1.23-0.65) |

Note-
$K_1$ = rate of FDG transport from blood to hepatic tissue.
[a]Low inflammation denoted by a histologic inflammation score of 3 or less.
[b]High inflammation denoted by a histologic inflammation score greater than 3.

With the use of dynamic FDG PET and advanced tracer kinetic modeling, and with the dual blood supply in the liver taken into consideration, the kinetic characteristics of glucose metabolism is exploited and the fundamental molecular process underlying hepatic glucose utilization is quantified on a regional basis. Dissecting the steps of the glucose uptake pathway enabled characterization in relation to histopathologic changes in NAFLD. Embodiments compare dynamic FDG PET findings with liver histologic findings. Specifically, the first step in the uptake pathway, the transport of FDG from plasma to intracellular compartment (K1), was significantly correlated with histologic inflammation. This correlation was also noted with the overall NAFLD activity score (NAS) for which a decrease in K1 was associated with increased NAS scores. A combination of insulin resistance, increased intrahepatic fat (presumably resulting in decreased liver blood flow), and disease progression with fibrous tissue deposition, collagen deposition, or both may lead to the decrease in K1 with worsening of the disease state. The parameter k3, which is representative of phosphorylation, increased with a change in inflammation. An increase in the glucose phosphorylation rate has been noted with increased steatosis, and it can be affected by insulin sensitivity. Methods discussed herein called for control of exogenous insulin by abstain from taking their overnight dose of long-acting insulin, morning dose of short-acting insulin, or both doses, although none of the patients in this cohort were taking insulin. Eight patients (seven patients with diabetes and one with apparent hyperinsulinemia) were taking metformin, and their K1 values were unaffected.

The current clinical use of FDG PET is mainly limited to static PET protocols that examine tracer spatial distribution at a late point in time (commonly 60 minutes after FDG injection), providing the standardized uptake value (SUV) as a semiquantitative measure of glucose utilization. The static FDG PET may be used for studying physiologic liver modeling. These kinetic parameters derived from dynamic FDG PET represent the underlying molecular processes of the uptake and trapping of FDG in the liver that may better characterize the status of liver disease.

Dynamic PET provides noninvasive three-dimensional images in real-time (as such, four dimensions (4-D)) changes of metabolic processes and enables studies of regional differences within organs. With advanced tracer kinetic modeling considering dual blood-supply in the liver, the kinetic characteristics of glucose metabolism can be exploited and the fundamental molecular process underlying hepatic glucose utilization may be quantified. Utilizing these benefits, $^{18}$F-FDG PET uptake kinetics in the liver serve as a tool for the determining changes in hepatic inflammation and steatosis in patients with non-alcoholic fatty liver disease in correlation with liver biopsy.

The hepatic glucose uptake decreases with worsening disease in NAFLD. The first step of the uptake pathway, or the transport of FDG from plasma to intracellular compartment (FDG-$K_1$) is significantly correlated with histologic inflammation. This correlation was also noted with the overall NAFLD activity score (NAS)—decrease in $K_1$ was associated with increased NAS scores. The correlation between the other micro-kinetic parameters of glucose uptake and phosphorylation/dephosphorylation are considered herein. These parameters show a trend towards either increasing (phosphorylation) or decreasing (release) with change in inflammation. Increased glucose phosphorylation rate has been noted with increased steatosis. It is essential to consider that FDG uptake maybe affected with changes in insulin sensitivity or exogenous insulin administration. Exogenous insulin was controlled by holding overnight long-acting and/or morning short-acting insulin, although none of the patients in this cohort were on insulin. Four patients were on metformin (three patients with diabetes and one was initiated for apparent hyperinsulinemia) and their $K_1$ values were unaffected.

In view of studies showing perceived heterogeneity of liver especially as noted in diseases such as NAFLD/NASH, the kinetics in eight of the nine liver segments (except the caudate lobe) are measured. Firstly, there was heterogeneity of FDG uptake kinetics across the segments of the liver. This shows the ability of FDG-PET to determine changes in glucose uptake in each segment in the entire liver and moreover shows the heterogeneity of NASH. Each individual patient had a unique variability pattern. This variability may very well be affected by diurnal changes or other extraneous factors that can affect FDG uptake. The heterogeneity may be, at least in part, caused by differences in the vascular supply, because each segment showed a distinct pattern of uptake kinetics. Secondly, although there was heterogeneity, the mean values of $K_1$ for each segment for the patients when analyzed by high or low inflammation/NAS groups, showed a clear distinction of FDG-uptake dependent on the level of inflammation. This would suggest that although there is heterogeneity in disease distribution, as the disease progresses all segments are affected and leads to overall physiologic changes across all the liver segments. The heterogeneity, at least in part, may be due to differences in vascular supply as each segment showed a distinct pattern of uptake kinetics.

As steatosis remains an essential component of NASH, FDG kinetic parameters that correlated with steatosis are discussed above. SUVR (SUV ratio of liver over a blood region) is used to reduce the effect of body factors. The SUVR was inversely correlated with hepatic steatosis as noted by liver biopsy and MR-PDFF, again supporting the concept of decreased hepatic glucose uptake with increasing steatosis. There exists a stronger correlation with MR-PDFF value and this maybe reflective of the fat fraction been calculated from a larger liver mass than what would be sampled in a biopsy.

Embodiments use $^{18}$F-FDG PET scan as a tool for detection and quantitation of changes in hepatic inflammation. The ability to co-detect steatosis and inflammation may fill an essential gap in the field for the diagnosis of NASH.

What is claimed is:

1. A method of determining a plurality of kinetic parameters associated with a kinetic model of an imaging agent in a liver, performed by an image reconstruction device, the method comprising:
receiving a plurality of imaging agent activities based on tracer transport kinetic imaging of the imaging agent in the liver during a predetermined time period;
generating a liver time activity curve and a circulatory input function based on the plurality of imaging agent activities;
jointly determining, based on the liver time activity curve and the circulatory input function, the plurality of kinetic parameters associated with the kinetic model of the imaging agent in the liver, wherein the plurality of kinetic parameters comprise at least two of a fractional blood volume, a blood to hepatic tissue rate, a hepatic tissue to blood rate, a phosphorylation rate, a dephosphorylation rate, a portal vein rate, and a hepatic artery fraction; and
generating an output characterizing liver inflammation in the liver at least based on the plurality of kinetic parameters.

2. The method of claim 1, further comprising:
determining a first set of imaging agent activities among the plurality of imaging agent activities, wherein the first set of imaging agent activities corresponds to one or more liver regions of interest;
determining a second set of imaging agent activities among the plurality of imaging agent activities, wherein the second set of imaging agent activities corresponds to one or more circulatory regions of interest;
determining, based on the first set of imaging agent activities, the liver time activity curve; and
determining, based on the second set of imaging agent activities, the circulatory input function, wherein the output characterizing the liver inflammation in the liver is generated based on the liver time activity curve and the circulatory input function.

3. The method of claim 2, wherein the one or more liver regions of interest correspond to one or more volumes of liver tissue and wherein the one or more circulatory regions of interest correspond to one or more volumes of circulatory tissue.

4. The method of claim 1, further comprising:
determining a liver standardized uptake value based on an injected dose of the imaging agent, the plurality of imaging agent activities, and a weight;
determining a liver standardized uptake value ratio based on the liver standardized uptake value and a blood standardized uptake value; and
determining one or more hepatic scores based on at least one of the plurality of kinetic parameters and the liver standardized uptake value ratio, wherein the one or more hepatic scores comprise one or more of a hepatic inflammation score, a hepatic steatosis score, and a hepatic fibrosis score.

5. The method of claim 4, further comprising:
comparing the one or more hepatic scores against one or more threshold scores; and
issuing an alert if any of the one or more hepatic scores exceeds the one or more threshold scores, wherein the alert indicates at least one hepatic score of the one or more hepatic scores that exceeds a corresponding threshold score of the one or more threshold scores, wherein the alert comprises one or more of the following: an audio tone or message, a graphical display, and an electronic message sent to a server computer.

6. The method of claim 1, wherein the predetermined time period comprises a plurality of time frames, and wherein each imaging agent activity of the plurality of imaging agent activities corresponds to a timeframe of the plurality of time frames and a volume of tissue.

7. The method of claim 1, wherein the plurality of imaging agent activities are determined using positron emission tomography (PET).

8. The method of claim 1, wherein the imaging agent is a radiotracer including $^{18}$F-fludeoxyglucose.

9. The method of claim 1, further comprising:
determining the kinetic model of the imaging agent in the liver as a compartmentalized model, the kinetic model including an imaging agent in plasma compartment, an imaging agent in hepatic tissue cells compartment, and a metabolized imaging agent compartment.

10. The method of claim 1, further comprising:
estimating a plurality of voxel-based kinetic parameters for each voxel of the plurality of imaging agent activities;
generating a parametric map of the plurality of voxel-based kinetic parameters; and
estimating the plurality of kinetic parameters from the parametric map of the plurality of kinetic parameters.

11. A system comprising an image reconstruction device comprising:

a processor; and a non-transitory computer readable medium coupled to the processor, the non-transitory computer readable medium comprising code executable by the processor for determining a plurality of kinetic parameters associated with a kinetic model of an imaging agent in a liver, performed by an image reconstruction device, wherein the code, when executed by the processor, causes the processor to:

receive a plurality of imaging agent activities based on tracer transport kinetic imaging of the imaging agent in the liver during a predetermined time period;

generate a liver time activity curve and a circulatory input function based on the plurality of imaging agent activities;

jointly determine, based on the liver time activity curve and the circulatory input function, the plurality of kinetic parameters associated with the kinetic model of the imaging agent in the liver, wherein the plurality of kinetic parameters comprise at least two of a fractional blood volume, a blood to hepatic tissue rate, a hepatic tissue to blood rate, a phosphorylation rate, a dephosphorylation rate, a portal vein rate, and a hepatic artery fraction; and generate an output characterizing liver inflammation in the liver at least based on the plurality of kinetic parameters.

12. The system of claim 11, further comprising:
a scanning device; and
a coincidence processing device, wherein the image reconstruction device receives the plurality of imaging agent activities from the coincidence processing device.

13. The system of claim 11, wherein the code, when executed by the processor, further causes the processor to:
determine a first set of imaging agent activities among the plurality of imaging agent activities, wherein the first set of imaging agent activities corresponds to one or more liver regions of interest;
determine a second set of imaging agent activities among the plurality of imaging agent activities, wherein the second set of imaging agent activities corresponds to one or more circulatory regions of interest;
determine, based on the first set of imaging agent activities, the liver time activity curve; and
determine, based on the second set of imaging agent activities, the circulatory input function, wherein the output characterizing the liver inflammation in the liver is generated based on the liver time activity curve and the circulatory input function.

14. The system of claim 13, wherein the one or more liver regions of interest correspond to one or more volumes of liver tissue and wherein the one or more circulatory regions of interest correspond to one or more volumes of circulatory tissue.

15. The system of claim 11, wherein the code, when executed by the processor, further causes the processor to:
determine a liver standardized uptake value based on an injected dose of the imaging agent, the plurality of imaging agent activities, and a weight;
determine a liver standardized uptake value ratio based on the liver standardized uptake value and a blood standardized uptake value; and
determine one or more hepatic scores based on at least one of the plurality of kinetic parameters and the liver standardized uptake value ratio, wherein the one or more hepatic scores comprise one or more of a hepatic inflammation score, a hepatic steatosis score, and a hepatic fibrosis score.

16. The system of claim 15, wherein the code, when executed by the processor, further causes the processor to:
compare the one or more hepatic scores against one or more threshold scores; and
issue an alert if any of the one or more hepatic scores exceeds the one or more threshold scores, wherein the alert indicates at least one hepatic score of the one or more hepatic scores that exceeds a corresponding threshold score of the one or more threshold scores, wherein the alert comprises one or more of the following: an audio tone or message, a graphical display, and an electronic message sent to a server computer.

17. The system of claim 11, wherein the predetermined time period comprises a plurality of time frames, and wherein each imaging agent activity of the plurality of imaging agent activities corresponds to a timeframe of the plurality of time frames and a volume of tissue.

18. The system of claim 11, wherein the plurality of imaging agent activities are determined using positron emission tomography (PET).

19. The system of claim 11, wherein the imaging agent is a radiotracer including $^{18}$F-fludeoxyglucose.

* * * * *